US010201310B2

(12) United States Patent
Mauri et al.

(10) Patent No.: US 10,201,310 B2
(45) Date of Patent: Feb. 12, 2019

(54) CALIBRATION PACKAGING APPARATUSES FOR PHYSIOLOGICAL MONITORING GARMENTS

(71) Applicant: L.I.F.E. Corporation S.A., Luxembourg (LU)

(72) Inventors: Marco Lorenzo Mauri, Brugheric (IT); Marco Giovanelli, Legnano (IT); Gianluigi Longinotti-Buitoni, Riverside, CT (US); Rudy Rigoni, Merate (IT)

(73) Assignee: L.I.F.E. Corporation S.A., Luxembourg (LU)

( * ) Notice: Subject to any disclaimer, the term of this patent is extended or adjusted under 35 U.S.C. 154(b) by 236 days.

(21) Appl. No.: 15/335,403

(22) Filed: Oct. 26, 2016

(65) Prior Publication Data
US 2017/0112440 A1    Apr. 27, 2017

Related U.S. Application Data

(60) Provisional application No. 62/246,404, filed on Oct. 26, 2015.

(51) Int. Cl.
*A61B 5/00* (2006.01)
*A61B 5/01* (2006.01)
*A61B 5/11* (2006.01)

(52) U.S. Cl.
CPC .............. *A61B 5/6804* (2013.01); *A61B 5/01* (2013.01); *A61B 5/11* (2013.01); *A61B 5/6898* (2013.01);
(Continued)

(58) Field of Classification Search
CPC .......... A61B 5/6804; A61B 5/01; A61B 5/11; A61B 5/6898; A61B 2560/0223;
(Continued)

(56) References Cited

U.S. PATENT DOCUMENTS 3,591,526 A   7/1971  Kawashima
3,793,716 A   2/1974  Smith Johannsen
(Continued)

FOREIGN PATENT DOCUMENTS

EP   1057923 A1   12/2000
EP   1335831 A1    8/2003
(Continued)

OTHER PUBLICATIONS

Longinotti Buitoni et al.; U.S. Appl. No. 15/813,073 entitled "Garments having stretchable and conductive ink," filed Nov. 14, 2017.
(Continued)

*Primary Examiner* — An T Nguyen
(74) *Attorney, Agent, or Firm* — Shay Glenn LLP

(57) ABSTRACT

A calibration packaging apparatus for a physiological monitoring garment is disclosed. The apparatus comprises a chamber to hold a physiological monitoring garment with a plurality of position sensors, motion sensors, or position and motion sensors. The apparatus is configured to calibrate the plurality of position sensors, motion sensors, or position and motion sensors simultaneously during a calibration process in which the apparatus is moved through a predetermined pattern and/or a random pattern. Methods of calibrating using the apparatus are also disclosed.

38 Claims, 22 Drawing Sheets

(52) U.S. Cl.
CPC .......... *A61B 2560/0223* (2013.01); *A61B 2562/0219* (2013.01)

(58) Field of Classification Search
CPC ... A61B 2562/0219; A64C 3/00; A64C 3/004; A64C 3/007; A64C 3/008; A64C 13/03; B65H 18/08; A47G 25/14; A63B 21/4037
See application file for complete search history.

(56) References Cited

U.S. PATENT DOCUMENTS

| | | |
|---|---|---|
| 4,624,817 A | 11/1986 | Gusack et al. |
| 4,710,981 A | 12/1987 | Sanchez |
| 4,823,240 A | 4/1989 | Shenker |
| 4,867,166 A | 9/1989 | Axelgaard et al. |
| 5,036,865 A | 8/1991 | Keaton |
| 5,111,818 A | 5/1992 | Suzuki et al. |
| 5,148,002 A | 9/1992 | Kuo et al. |
| 5,163,006 A | 11/1992 | Deziel |
| 5,241,300 A | 8/1993 | Buschmann |
| 5,280,265 A | 1/1994 | Kramer et al. |
| 5,352,315 A | 10/1994 | Carrier et al. |
| 5,379,461 A | 1/1995 | Wilmers |
| 5,395,508 A | 3/1995 | Jolly et al. |
| 5,557,263 A | 9/1996 | Fisher et al. |
| 5,581,492 A | 12/1996 | Janik |
| 5,635,909 A | 6/1997 | Cole |
| 5,678,448 A | 10/1997 | Fullen et al. |
| 5,694,645 A | 12/1997 | Triplette |
| 5,749,365 A | 5/1998 | Magill |
| 5,802,607 A | 9/1998 | Triplette |
| 5,824,996 A | 10/1998 | Kochman et al. |
| 5,845,644 A | 12/1998 | Hughes et al. |
| 5,853,005 A | 12/1998 | Scanlon |
| 5,865,740 A | 2/1999 | Kelly et al. |
| 5,903,222 A | 5/1999 | Kawarizadeh et al. |
| 5,906,004 A | 5/1999 | Lebby et al. |
| 5,912,653 A | 6/1999 | Fitch |
| 5,921,674 A | 7/1999 | Koczi |
| 5,984,063 A * | 11/1999 | Wallace III ............ A45C 13/03 190/109 |
| 6,016,476 A | 1/2000 | Maes et al. |
| 6,019,877 A | 2/2000 | Dupelle et al. |
| 6,024,575 A | 2/2000 | Ulrich |
| 6,047,203 A | 4/2000 | Sackner et al. |
| 6,080,690 A | 6/2000 | Lebby et al. |
| 6,097,297 A | 8/2000 | Fard |
| 6,136,127 A | 10/2000 | De Bastiani |
| 6,144,120 A | 11/2000 | Doi et al. |
| 6,210,771 B1 | 4/2001 | Post et al. |
| 6,232,879 B1 | 5/2001 | Tyren |
| 6,259,399 B1 | 7/2001 | Krasner |
| 6,319,015 B1 | 11/2001 | Faunce |
| 6,325,066 B1 | 12/2001 | Hughes et al. |
| 6,341,504 B1 | 1/2002 | Istook |
| 6,349,201 B1 | 2/2002 | Ford |
| 6,415,176 B1 | 7/2002 | Scheirer et al. |
| 6,436,064 B1 | 8/2002 | Kloecker |
| 6,490,534 B1 | 12/2002 | Pfister |
| 6,561,814 B2 | 5/2003 | Tilbury et al. |
| 6,563,424 B1 | 5/2003 | Kaario |
| 6,642,467 B2 | 11/2003 | Farringdon |
| 6,668,380 B2 | 12/2003 | Marmaropolous et al. |
| 6,713,733 B2 | 3/2004 | Kochman et al. |
| 6,729,025 B2 | 5/2004 | Farrell et al. |
| 6,792,124 B2 | 9/2004 | Tilbury et al. |
| 6,801,140 B2 | 10/2004 | Mantyjarvi et al. |
| 6,830,344 B2 | 12/2004 | Reho et al. |
| 6,895,261 B1 | 5/2005 | Palamides |
| 6,930,608 B2 | 8/2005 | Grajales et al. |
| 6,968,075 B1 | 11/2005 | Chang |
| 6,970,731 B1 | 11/2005 | Jayaraman et al. |
| 6,982,115 B2 | 1/2006 | Poulos et al. |
| 7,020,508 B2 | 3/2006 | Stivoric et al. |
| 7,034,685 B2 | 4/2006 | Fabre et al. |
| 7,161,084 B2 | 1/2007 | Sandbach |
| 7,173,437 B2 | 2/2007 | Hervieux et al. |
| 7,191,803 B2 | 3/2007 | Orr et al. |
| 7,210,939 B2 | 5/2007 | Marmaropolous et al. |
| 7,211,053 B2 | 5/2007 | Marmaropolous et al. |
| 7,230,610 B2 | 6/2007 | Jung et al. |
| 7,248,756 B2 | 7/2007 | Ebbesen et al. |
| 7,250,547 B1 | 7/2007 | Hofmeister et al. |
| 7,299,034 B2 | 11/2007 | Kates |
| 7,299,964 B2 | 11/2007 | Jayaraman et al. |
| 7,319,895 B2 | 1/2008 | Klefstad-Sillonville et al. |
| 7,320,947 B2 | 1/2008 | Child et al. |
| 7,321,785 B2 | 1/2008 | Harris |
| 7,324,841 B2 | 1/2008 | Reho et al. |
| 7,344,379 B2 | 3/2008 | Marmaropolous et al. |
| 7,348,645 B2 | 3/2008 | Xu |
| 7,365,031 B2 | 4/2008 | Swallow et al. |
| 7,377,133 B2 | 5/2008 | Sandbach et al. |
| 7,388,166 B2 | 6/2008 | Marmaropolous et al. |
| 7,429,959 B2 | 9/2008 | Gerder et al. |
| 7,448,874 B2 | 11/2008 | Willis |
| 7,476,104 B2 | 1/2009 | Marmaropolous et al. |
| 7,559,768 B2 | 7/2009 | Marmaropolous et al. |
| 7,578,195 B2 | 8/2009 | DeAngelis et al. |
| 7,616,112 B2 | 11/2009 | Miller, III |
| 7,645,220 B2 | 1/2010 | Hoffman et al. |
| 7,665,288 B2 | 2/2010 | Karayianni et al. |
| 7,683,643 B2 | 3/2010 | Qi et al. |
| 7,712,373 B2 | 5/2010 | Nagle et al. |
| 7,715,873 B1 | 5/2010 | Biere et al. |
| 7,719,007 B2 | 5/2010 | Thompkins et al. |
| 7,732,002 B2 | 6/2010 | Kodas et al. |
| 7,753,685 B2 | 7/2010 | Lee et al. |
| 7,753,845 B2 | 7/2010 | Gopinathan et al. |
| 7,760,082 B2 | 7/2010 | Wong et al. |
| 7,769,412 B1 | 8/2010 | Gailloux |
| 7,770,473 B2 | 8/2010 | Von Lilienfeld-Toal et al. |
| 7,779,656 B2 | 8/2010 | Dias et al. |
| 7,783,334 B2 | 8/2010 | Nam et al. |
| 7,787,726 B2 | 8/2010 | Ten Eyck et al. |
| 7,849,888 B2 | 12/2010 | Karayianni et al. |
| 7,862,624 B2 | 1/2011 | Tran |
| 7,870,761 B2 | 1/2011 | Valentine et al. |
| 7,872,557 B2 | 1/2011 | Seibert |
| 7,878,030 B2 | 2/2011 | Burr |
| 7,880,607 B2 | 2/2011 | Olson et al. |
| 7,891,020 B2 | 2/2011 | Von Bluecher |
| 7,914,108 B2 | 3/2011 | Konno et al. |
| 7,933,554 B2 | 4/2011 | Hoyt et al. |
| 7,955,696 B2 | 6/2011 | Baikerikar et al. |
| 7,976,480 B2 | 7/2011 | Grajales et al. |
| 7,982,613 B2 | 7/2011 | Zheng |
| 7,983,876 B2 | 7/2011 | Vock et al. |
| 8,008,606 B2 | 8/2011 | Kaiserman et al. |
| 8,024,023 B2 | 9/2011 | Tolvanen |
| 8,032,199 B2 | 10/2011 | Linti et al. |
| 8,063,307 B2 | 11/2011 | Bukshpun et al. |
| 8,099,258 B2 | 1/2012 | Alten et al. |
| 8,140,143 B2 | 3/2012 | Picard et al. |
| 8,146,171 B2 | 4/2012 | Chung et al. |
| 8,162,857 B2 | 4/2012 | Lanfermann et al. |
| 8,186,231 B2 | 5/2012 | Graumann et al. |
| 8,214,008 B2 | 7/2012 | Hassonjee et al. |
| 8,228,202 B2 | 7/2012 | Buchner et al. |
| 8,253,586 B1 | 8/2012 | Matak |
| 8,262,217 B2 | 9/2012 | Furukawa |
| 8,263,215 B2 | 9/2012 | Burr et al. |
| 8,267,862 B2 | 9/2012 | Jeong et al. |
| 8,308,489 B2 | 11/2012 | Lee et al. |
| 8,331,097 B2 | 12/2012 | Yang et al. |
| 8,340,740 B2 | 12/2012 | Holzer et al. |
| 8,348,841 B2 | 1/2013 | Varadan |
| 8,348,865 B2 | 1/2013 | Jeong et al. |
| 8,362,882 B2 | 1/2013 | Heubel et al. |
| 8,373,079 B2 | 2/2013 | Walkington |
| 8,398,546 B2 | 3/2013 | Pacione et al. |
| 8,403,845 B2 | 3/2013 | Stivoric et al. |
| 8,416,579 B2 | 4/2013 | Biesheuvel et al. |
| 8,475,371 B2 | 7/2013 | Derchak et al. |

(56) References Cited

U.S. PATENT DOCUMENTS

| | | |
|---|---|---|
| 8,739,397 B2 | 6/2014 | Nagata et al. |
| 8,862,431 B2 | 10/2014 | Hodge |
| 8,925,393 B2 | 1/2015 | Cannard et al. |
| 8,945,328 B2 | 2/2015 | Longinotti-Buitoni et al. |
| 8,948,839 B1 | 2/2015 | Longinotti-Buitoni et al. |
| 8,954,129 B1 | 2/2015 | Schlegel et al. |
| 9,282,893 B2 | 3/2016 | Longinotti-Buitoni et al. |
| 9,566,032 B2 | 2/2017 | Babaeizadeh et al. |
| 9,979,547 B2 | 5/2018 | Starner et al. |
| 10,039,354 B2 * | 8/2018 | Van der Laan ........ A45C 3/004 |
| 2002/0093515 A1 | 7/2002 | Fay et al. |
| 2003/0139692 A1 | 7/2003 | Barrey et al. |
| 2004/0115430 A1 | 6/2004 | Leonard |
| 2004/0249242 A1 | 12/2004 | Lau et al. |
| 2005/0029680 A1 | 2/2005 | Jung et al. |
| 2005/0058744 A1 | 3/2005 | Steinberg et al. |
| 2005/0067816 A1 | 3/2005 | Buckman |
| 2005/0107722 A1 | 5/2005 | Ozaki et al. |
| 2005/0228234 A1 | 10/2005 | Yang |
| 2006/0007059 A1 | 1/2006 | Bell |
| 2006/0062993 A1 | 3/2006 | Ogata et al. |
| 2006/0080182 A1 | 4/2006 | Thompson et al. |
| 2006/0124470 A1 | 6/2006 | Zama et al. |
| 2006/0139165 A1 | 6/2006 | Bader |
| 2006/0155182 A1 | 7/2006 | Mazzarolo |
| 2007/0000912 A1 | 1/2007 | Aisenbrey |
| 2007/0046720 A1 | 3/2007 | Konno et al. |
| 2007/0049842 A1 | 3/2007 | Hill et al. |
| 2007/0151312 A1 | 7/2007 | Bruce et al. |
| 2007/0153363 A1 | 7/2007 | Gruner |
| 2007/0177770 A1 | 8/2007 | Derchak et al. |
| 2007/0178716 A1 | 8/2007 | Glaser et al. |
| 2007/0202765 A1 | 8/2007 | Krans et al. |
| 2007/0293781 A1 | 12/2007 | Sims et al. |
| 2008/0045815 A1 | 2/2008 | Derchak et al. |
| 2008/0058744 A1 | 3/2008 | Tippey et al. |
| 2008/0064964 A1 | 3/2008 | Nagata et al. |
| 2008/0083720 A1 | 4/2008 | Gentile et al. |
| 2008/0083721 A1 | 4/2008 | Kaiserman et al. |
| 2008/0083740 A1 | 4/2008 | Kaiserman et al. |
| 2008/0171914 A1 | 7/2008 | Ouwerkerk et al. |
| 2008/0177168 A1 | 7/2008 | Callahan et al. |
| 2008/0234561 A1 | 9/2008 | Roesicke et al. |
| 2008/0241391 A1 | 10/2008 | Kim et al. |
| 2008/0246629 A1 | 10/2008 | Tsui et al. |
| 2008/0255794 A1 | 10/2008 | Levine |
| 2008/0258921 A1 | 10/2008 | Woo et al. |
| 2008/0269629 A1 | 10/2008 | Reiner |
| 2008/0269652 A1 | 10/2008 | Reiner |
| 2008/0287769 A1 | 11/2008 | Kurzweil et al. |
| 2008/0287770 A1 | 11/2008 | Kurzweil et al. |
| 2008/0294019 A1 | 11/2008 | Tran |
| 2009/0012408 A1 | 1/2009 | Nagata et al. |
| 2009/0018410 A1 | 1/2009 | Coene et al. |
| 2009/0105795 A1 | 4/2009 | Minogue et al. |
| 2009/0112078 A1 | 4/2009 | Tabe |
| 2009/0157327 A1 | 6/2009 | Nissila |
| 2009/0227856 A1 | 9/2009 | Russell et al. |
| 2009/0281394 A1 | 11/2009 | Russell et al. |
| 2009/0286055 A1 | 11/2009 | Pourdeyhimi et al. |
| 2010/0004720 A1 | 1/2010 | Li et al. |
| 2010/0029598 A1 | 2/2010 | Kopitz et al. |
| 2010/0041974 A1 | 2/2010 | Ting et al. |
| 2010/0059274 A1 | 3/2010 | Ives et al. |
| 2010/0071205 A1 | 3/2010 | Graumann et al. |
| 2010/0077528 A1 | 4/2010 | Lind et al. |
| 2010/0112195 A1 | 5/2010 | Kodas et al. |
| 2010/0113910 A1 | 5/2010 | Brauers et al. |
| 2010/0149567 A1 | 6/2010 | Kanazawa et al. |
| 2010/0185062 A1 | 7/2010 | Salazar et al. |
| 2010/0185398 A1 | 7/2010 | Berns et al. |
| 2010/0194815 A1 | 8/2010 | Furukawa |
| 2010/0198038 A1 | 8/2010 | Nagata et al. |
| 2010/0234715 A1 | 9/2010 | Shin et al. |
| 2010/0274100 A1 | 10/2010 | Behar et al. |
| 2010/0292598 A1 | 11/2010 | Roschk et al. |
| 2010/0309209 A1 | 12/2010 | Hodgins et al. |
| 2010/0312071 A1 | 12/2010 | Schenk |
| 2010/0324405 A1 | 12/2010 | Niemi et al. |
| 2011/0000412 A1 | 1/2011 | Chung et al. |
| 2011/0015498 A1 | 1/2011 | Mestrovic et al. |
| 2011/0032103 A1 | 2/2011 | Bhat et al. |
| 2011/0042125 A1 | 2/2011 | Lee et al. |
| 2011/0087115 A1 | 4/2011 | Sackner et al. |
| 2011/0092795 A1 | 4/2011 | Derchak |
| 2011/0100683 A1 | 5/2011 | Bhattacharya et al. |
| 2011/0102304 A1 | 5/2011 | Nelson |
| 2011/0115624 A1 | 5/2011 | Tran |
| 2011/0125064 A1 | 5/2011 | Shyr |
| 2011/0130643 A1 | 6/2011 | Derchak et al. |
| 2011/0144457 A1 | 6/2011 | Coulon |
| 2011/0183068 A1 | 7/2011 | Yamakawa et al. |
| 2011/0184270 A1 | 7/2011 | Russell et al. |
| 2011/0259638 A1 | 10/2011 | Sherrill et al. |
| 2011/0267578 A1 | 11/2011 | Wilson |
| 2011/0277206 A1 | 11/2011 | Sokolowski |
| 2011/0288605 A1 | 11/2011 | Kaib et al. |
| 2012/0024833 A1 | 2/2012 | Klewer et al. |
| 2012/0029299 A1 | 2/2012 | Deremer et al. |
| 2012/0030935 A1 | 2/2012 | Slade et al. |
| 2012/0031431 A1 | 2/2012 | Carlson et al. |
| 2012/0035426 A1 | 2/2012 | Mielcarz et al. |
| 2012/0071039 A1 | 3/2012 | Debock et al. |
| 2012/0071793 A1 | 3/2012 | Gal |
| 2012/0078127 A1 | 3/2012 | McDonald et al. |
| 2012/0088986 A1 | 4/2012 | David et al. |
| 2012/0118427 A1 | 5/2012 | Brookstein et al. |
| 2012/0127687 A1 | 5/2012 | Allee et al. |
| 2012/0136231 A1 | 5/2012 | Markel |
| 2012/0143093 A1 | 6/2012 | Stirling et al. |
| 2012/0144551 A1 | 6/2012 | Guldalian |
| 2012/0144561 A1 | 6/2012 | Begriche et al. |
| 2012/0144934 A1 | 6/2012 | Russell et al. |
| 2012/0146797 A1 | 6/2012 | Oskin et al. |
| 2012/0158074 A1 | 6/2012 | Hall |
| 2012/0165645 A1 | 6/2012 | Russell et al. |
| 2012/0165717 A1 | 6/2012 | Al Khaburi |
| 2012/0184826 A1 | 7/2012 | Keenan et al. |
| 2012/0188158 A1 | 7/2012 | Tan et al. |
| 2012/0197224 A1 | 8/2012 | Chagger |
| 2012/0215076 A1 | 8/2012 | Yang et al. |
| 2012/0223833 A1 | 9/2012 | Thomas et al. |
| 2012/0233751 A1 | 9/2012 | Hexels |
| 2012/0238845 A1 | 9/2012 | Yang |
| 2012/0246795 A1 | 10/2012 | Scheffler et al. |
| 2012/0255166 A1 | 10/2012 | Kim et al. |
| 2012/0324616 A1 | 12/2012 | Hyde et al. |
| 2012/0330109 A1 | 12/2012 | Tran |
| 2013/0013331 A1 | 1/2013 | Horseman |
| 2013/0019372 A1 | 1/2013 | Esses |
| 2013/0019383 A1 | 1/2013 | Korkala et al. |
| 2013/0041272 A1 | 2/2013 | Guillen et al. |
| 2013/0053674 A1 | 2/2013 | Volker |
| 2013/0066168 A1 | 3/2013 | Yang et al. |
| 2013/0072777 A1 | 3/2013 | Tremblay |
| 2013/0077263 A1 | 3/2013 | Oleson et al. |
| 2013/0079860 A1 | 3/2013 | Besio |
| 2013/0144111 A1 | 6/2013 | Wang et al. |
| 2013/0179288 A1 | 7/2013 | Moses et al. |
| 2013/0211208 A1 | 8/2013 | Varadan |
| 2013/0212900 A1 | 8/2013 | Stewart |
| 2013/0231711 A1 | 9/2013 | Kalb |
| 2013/0244121 A1 | 9/2013 | Gogotsi et al. |
| 2013/0245423 A1 | 9/2013 | Derchak et al. |
| 2013/0281795 A1 | 10/2013 | Varadan |
| 2013/0314668 A1 | 11/2013 | Haddadi et al. |
| 2014/0061273 A1 | 3/2014 | Bullivant et al. |
| 2014/0100436 A1 | 4/2014 | Brunner et al. |
| 2014/0135593 A1 | 5/2014 | Jayalth et al. |
| 2014/0172134 A1 | 6/2014 | Casillas et al. |
| 2014/0182880 A1 | 7/2014 | Simenhaus et al. |
| 2014/0206948 A1 | 7/2014 | Romem |
| 2014/0303470 A1 | 10/2014 | Tsukada et al. |
| 2014/0312027 A1 | 10/2014 | Augustine et al. |

(56) References Cited

U.S. PATENT DOCUMENTS

| | | | |
|---|---|---|---|
| 2015/0143601 A1 | 5/2015 | Longinotti-Buitoni et al. | |
| 2015/0250420 A1 | 9/2015 | Longinotti-Buitoni et al. | |
| 2015/0289820 A1 | 10/2015 | Miller et al. | |
| 2015/0342266 A1 | 12/2015 | Cooper et al. | |
| 2016/0262462 A1 | 9/2016 | Kawamura et al. | |
| 2016/0314576 A1 | 10/2016 | Aliverti et al. | |
| 2018/0000367 A1 | 1/2018 | Longinotti-Buitoni et al. | |
| 2018/0184735 A1 | 7/2018 | Longinotti-Buitoni et al. | |
| 2018/0199635 A1 | 7/2018 | Longinotti-Buitoni et al. | |

FOREIGN PATENT DOCUMENTS

| | | | |
|---|---|---|---|
| EP | 1478249 A1 | 11/2004 | |
| EP | 1509128 A1 | 3/2005 | |
| EP | 1622512 A2 | 2/2006 | |
| EP | 1709903 A1 | 10/2006 | |
| EP | 1905112 A2 | 4/2008 | |
| EP | 1907075 A2 | 4/2008 | |
| EP | 1925718 A2 | 5/2008 | |
| EP | 2025369 A2 | 2/2009 | |
| EP | 2191737 A1 | 6/2010 | |
| EP | 2196142 A1 | 6/2010 | |
| EP | 2217145 A1 | 8/2010 | |
| EP | 2314744 A2 | 4/2011 | |
| EP | 3037036 A1 | 6/2016 | |
| WO | WO 90/06189 A1 | 6/1990 | |
| WO | WO 00/16493 A1 | 3/2000 | |
| WO | WO 01/01855 A1 | 1/2001 | |
| WO | WO03/000015 A2 | 1/2003 | |
| WO | WO 03/060449 A1 | 7/2003 | |
| WO | WO 2004/076731 A1 | 9/2004 | |
| WO | WO 2004/107831 A2 | 12/2004 | |
| WO | WO 2005/032447 A2 | 4/2005 | |
| WO | WO 2005/067796 A1 | 7/2005 | |
| WO | WO 2005/096133 A1 | 10/2005 | |
| WO | WO 2006/064447 A2 | 6/2006 | |
| WO | WO 2006/102538 A2 | 9/2006 | |
| WO | WO 2007/056557 A1 | 5/2007 | |
| WO | WO 2008/137046 A1 | 11/2008 | |
| WO | WO 2008/153786 A1 | 12/2008 | |
| WO | WO 2009/040696 A1 | 4/2009 | |
| WO | WO 2009/112281 A1 | 9/2009 | |
| WO | WO 2010/038176 A1 | 4/2010 | |
| WO | WO 2010/044018 A1 | 4/2010 | |
| WO | WO 2010/058346 A2 | 5/2010 | |
| WO | WO 2010/085671 A1 | 7/2010 | |
| WO | WO 2010/085688 A1 | 7/2010 | |
| WO | WO2010/096907 A1 | 9/2010 | |
| WO | WO 2010/120945 A1 | 10/2010 | |
| WO | WO 2011/092620 A1 | 8/2011 | |
| WO | WO 2011/156095 A2 | 12/2011 | |
| WO | WO2012/011068 A1 | 1/2012 | |
| WO | WO 2012/060524 A1 | 5/2012 | |
| WO | WO 2012/066056 A1 | 5/2012 | |
| WO | WO 2012/073076 A1 | 6/2012 | |
| WO | WO 2012/073230 A1 | 6/2012 | |
| WO | WO 2012/083066 A2 | 6/2012 | |
| WO | WO 2012/104484 A1 | 8/2012 | |
| WO | WO 2012/110954 A1 | 8/2012 | |
| WO | WO 2012/112186 A1 | 8/2012 | |
| WO | WO 2012/113014 A1 | 8/2012 | |
| WO | WO 2012/140079 A1 | 10/2012 | |
| WO | WO 2012/140522 A2 | 10/2012 | |
| WO | WO 2012/168836 A2 | 12/2012 | |
| WO | WO 2012/176193 A1 | 12/2012 | |
| WO | WO 2014/025430 A2 | 2/2014 | |
| WO | WO 2014/075682 A1 | 5/2014 | |
| WO | WO 2014/204323 A1 | 12/2014 | |
| WO | WO 2015/103620 A1 | 7/2015 | |
| WO | WO 2015/138515 A1 | 9/2015 | |
| WO | WO2016/035350 A1 | 3/2016 | |

OTHER PUBLICATIONS

Hossain et al.; Human identity verification by using physiological and behavioural biometric traits; International Journal of Bioscience, Biochemistry and bioinformatics; 1(3); pp. 199-205; Sep. 2011.

Chourabi et al.; Understanding smart cities: An integrative framework; 45th Hawii International Conference on System Sciences; pp. 2289-2297; Jan. 4, 2012.

Purao et al.; Modeling citizen-centric services in smart cities; 32nd, International Conference on Conceptual Modeling; Hong Kong; pp. 438-445; (8 pages, retrieved from the internet at https://icity.smu.edu.sg/sites/icity.smu.edu.sg/files/publications/Modeling-Citizen-centric-Services-in-Smart-Cities_ER2013.pdf); Nov. 11-13, 2013.

Longinotti_Buitoni et al.; U.S. Appl. No. 15/554,784 entitled "Laundry system for smart garments," filed Aug. 31, 2017.

Aliverti et al.; Compartmental analysis of breathing in the supine and prone positions by optoelectronic plethysmography; Ann Biomed Eng; 29(1):60-70; Jan. 2001.

Babchenko et al.; Fiber optic sensor for the measurement of respiratory chest circumference changes; J Biomed Opt; 4(2):224-229; Apr. 1999.

Cala et al.; Chest wall and lung volume estimation by optical reflectance motion analysis; J Appl Physiol; 81(6):2680-2689; Dec. 1996.

Chadha et al.; Validation of respiratory inductive plethysmography using different calibration procedures; Am Rev Respir Dis; 125:644-649; Jun. 1982.

Chen et al.; Color structured light system of chest wall motion measurement for respiratory volume evaluation; J Biomed Opt; 15(2):026013; Mar.-Apr. 2010.

D'Angelo et al.; A system for respiratory motion detection using optical fibers embedded into textiles; Conf Proc IEEE Med Biol Soc; 3694-3697; Aug. 2008.

Dodgson; Variation and extrema of human interpupillary distance; Prod. of SPIE: Stereoscopic Displays and Virtual Reality Systems XI; vol. 5291; pp. 36-46; Jan. 2004.

Ferrigno et al.; Three-dimensional optical analysis of chest wall motion; J Appl Physiol; 77(3):1224-1231; Sep. 1994.

Gramse et al.; Novel concept for a noninvasive cardiopulmonary monitor for infants: a pair of pajamas with an integrated sensor module; Ann Biomed Eng; 31(2):152-158; Feb. 2003.

Heilman et al.; Accuracy of the LifeShirt (Vivometrics) in the detection of cardiac rhythms; Biol Psychol; 75(3):300-305; Jul. 2007.

Kenyon et al.; Rib cage mechanics during quiet breathing and exercise in humans; J Appl Physiol; 83(4):1242-1255; Oct. 1997.

Konno et al.; Measurement of the separate volume changes of rib cage and abdomen during breathing; J Appl Physiol; 22(3):407-422; Mar. 1967.

Lafortuna et al.; A new instrument for the measurement of rib cage and abdomen circumference variation in respiration at rest and during exercise; Eur J Appl Physiol Occup Physiol; 71(2-3):259-265; Mar. 1995.

Milledge et al.; Inductive plethysmography—a new respiratory transducer; J Physiol; 267(1):4P-5P; May 1977.

Peacock et al.; Optical mapping of the thoracoabdominal wall; Thorax; 39(2):93-100; Feb. 1984.

Peacock et al.; Optical measurement of the change in trunk volume with breathing; Bull Eur Physiopathol Respir; 21(2):125-129; Mar.-Apr. 1985.

Pennock B.E.; Rib cage and abdominal piezoelectric film belts to measure ventilatory airflow; J Clin Monit; 6(4):276-283; Oct. 1990.

Sackner et al.; Calibration of respiratory inductive plethysmograph during natural breathing; J Appl Physiol; 66(1):410-420; Jan. 1989.

Saumarez; Automated optical measurements of human torso surface movements during freathing; J. Appl. Physiol.; 60(2); pp. 702-709; Feb. 1986.

Zimmerman et al.; Postural changes in rib cage and abdominal volume-motion coefficients and their effect on the calibration of a respiratory inductance plethysmograph; Am Rev Respir Dis; 127(2):209-214; Feb. 1983.

Longinotti-Buitoni et al; U.S. Appl. No. 15/324,152 entitled "Garments having stretchable and conductive ink," filed Jan. 5, 2017.

(56) References Cited

OTHER PUBLICATIONS

Longinotti-Buitoni et al.; U.S. Appl. No. 15/516,138 entitled "Devices and methods for use with physiological monitoring garments," filed Mar. 31, 2017.

* cited by examiner

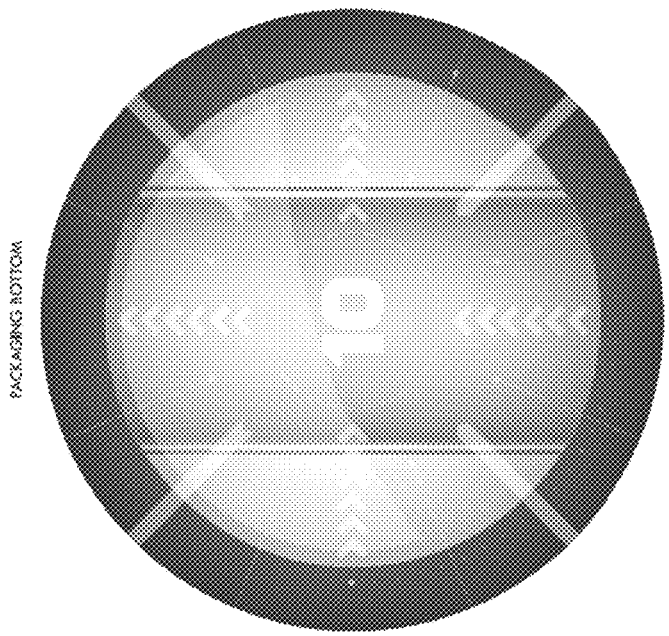
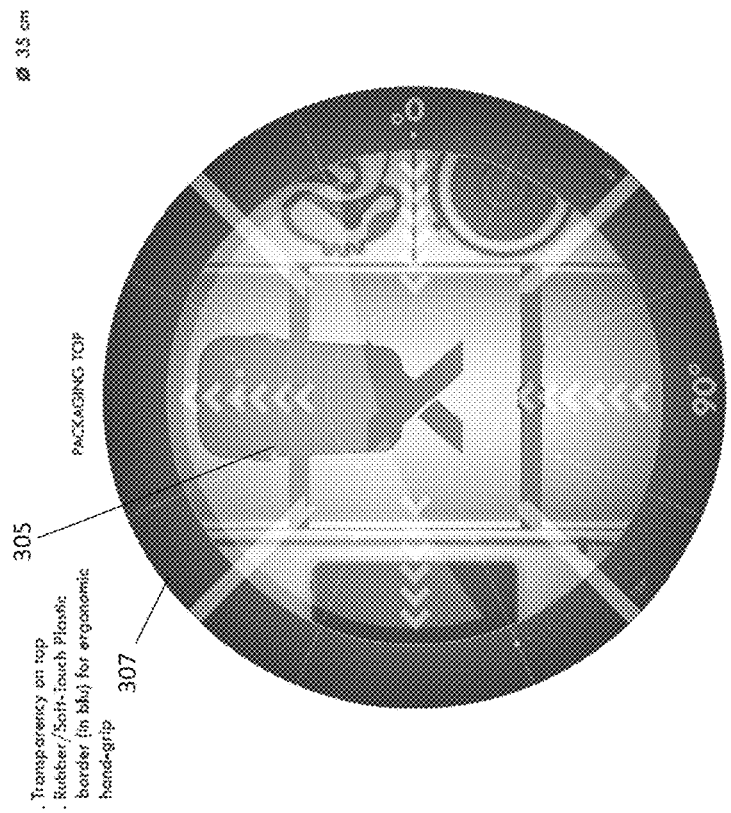
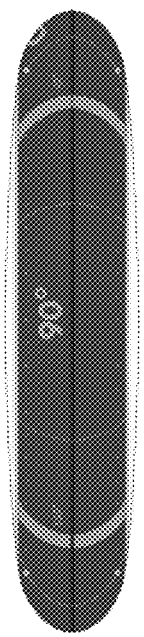
FIG. 3B
FIG. 3A
FIG. 3C

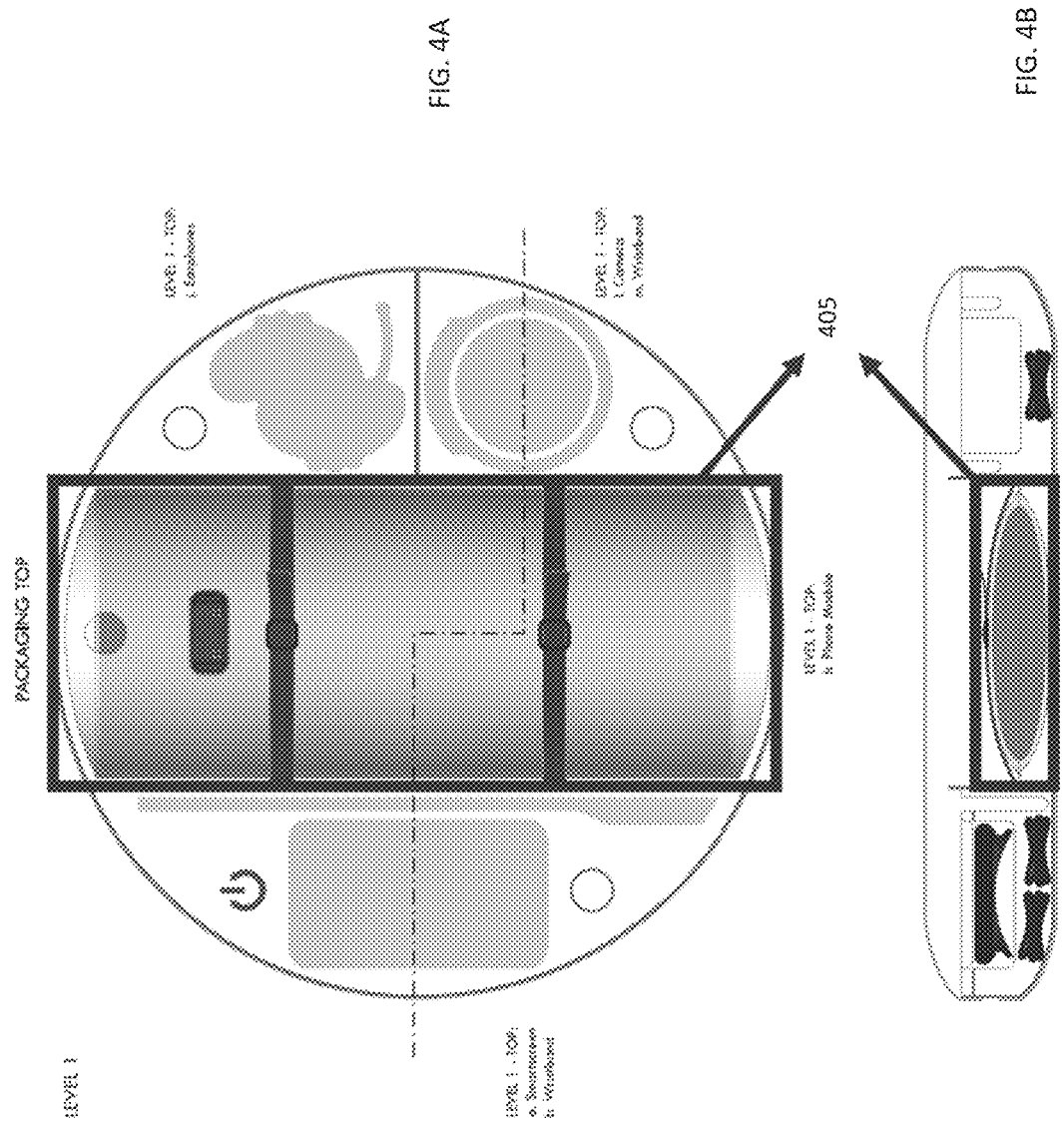

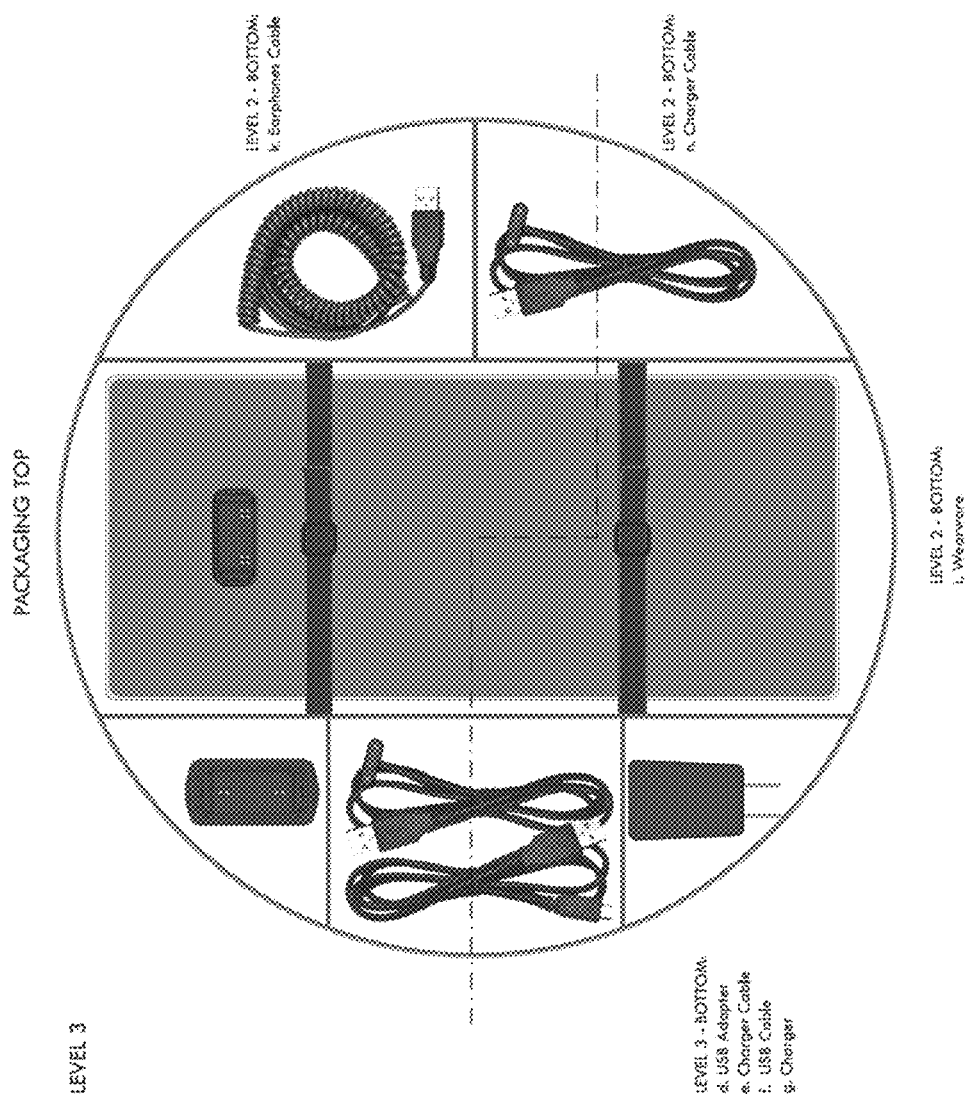

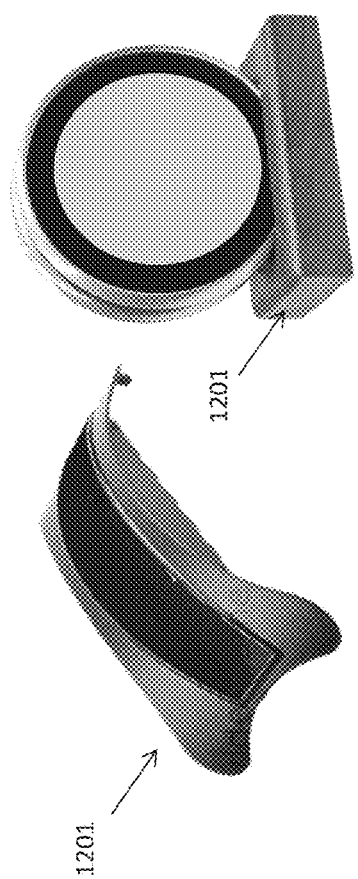
FIG. 12A
FIG. 12B
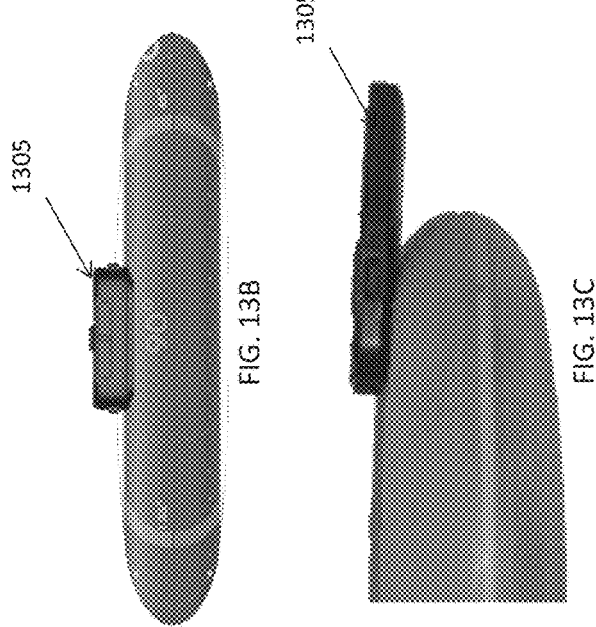
FIG. 13B
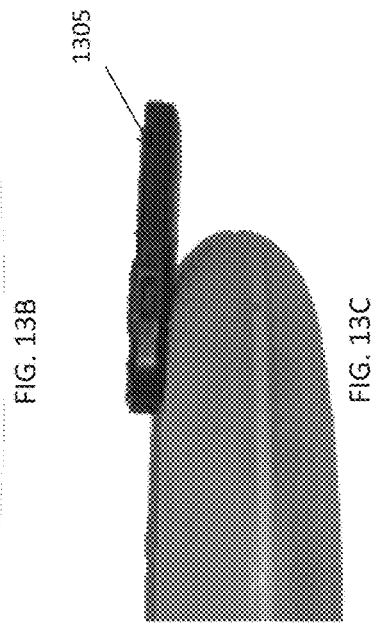
FIG. 13C
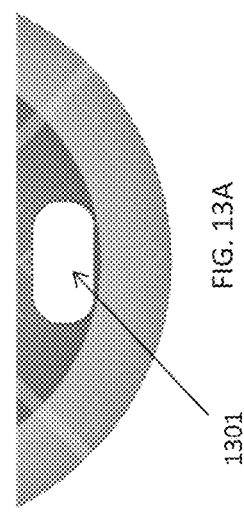
FIG. 13A

CALIBRATION PACKAGING APPARATUSES FOR PHYSIOLOGICAL MONITORING GARMENTS

CROSS REFERENCE TO RELATED APPLICATIONS

This patent application claims priority to U.S. Provisional Patent Application No. 62/246,404, filed on Oct. 26, 2015, titled, "CALIBRATION PACKAGING APPARATUS FOR PHYSIOLOGICAL MONITORING GARMENTS."

The apparatuses and methods described herein may be related to the following applications: U.S. patent application Ser. No. 14/023,830, filed on Sep. 11, 2013, titled "WEARABLE COMMUNICATION PLATFORM;" U.S. patent application Ser. No. 14/331,185, filed on Jul. 14, 2014, titled "METHODS OF MAKING GARMENTS HAVING STRETCHABLE AND CONDUCTIVE INK;" U.S. patent application Ser. No. 14/331,142, filed on Jul. 14, 2014, titled "COMPRESSION GARMENTS HAVING STRETCHABLE AND CONDUCTIVE INK;" U.S. Provisional Patent Application No. 61/699,440, filed on Sep. 11, 2012, titled "SMARTWEAR SYSTEM;" U.S. Provisional Patent Application No. 61/862,936, filed on Aug. 6, 2013, titled "WEARABLE COMMUNICATION PLATFORM;" and U.S. Provisional Patent Application No. 61/950,782, filed on Mar. 10, 2014, titled "PHYSIOLOGICAL MONITORING GARMENTS."

Each of the above applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are calibration boxes and packaging configured to be used with wearable physiological monitoring garments.

BACKGROUND

In the last twenty years, the development of mobile telecommunications devices have has dramatically expanded and modified the ways in which people communicate. Computers with ever-faster computer processors enabled faster communication with increased processing speed and improved analysis of vast quantities of data. In addition, sensor technology has also rapidly expanded how patients have been monitored, even by non-professionals. The development of various sensors enabled a variety of measurements to be taken and analyzed by a computer to generate useful information. In recent years, the use of medical sensing technology in combination with various communications platforms has provided new and interesting ways for people, including patients, to be monitored or to monitor themselves and communicate the results of the monitoring with their physician or caregiver. For example, mobile devices such as smart phones have enabled mobile device users to communicate remotely and provided some ability to obtain, analyze, use, and control information and data. For example, a mobile device user may be able to use application software (an "app") for various individualized tasks, such as recording their medical history in a defined format, playing a game, reading a book, etc. An app may work with a sensor in a mobile device to provide information that a user wants. For example, an app may work with an accelerometer in a smart phone and determine how far someone walked and how many calories were burned during the walk.

The use of a mobile communications platform such as a smartphone with one or more such biometric sensors has been described in various contexts. For example, U.S. Publication No. US2010/0029598 to Roschk et al. describes a "Device for Monitoring Physical Fitness" that is equipped with a heart rate monitor component for detecting heart rate data and an evaluation device for providing fitness information that can be displayed by a display device and is derived by a processing unit, embodied for reading in and including supplementary personal data. U.S. Publication No. US2009/0157327 to Nissila describes an "Electronic Device, Arrangement, and Method of Estimating Fluid Loss" that is equipped with "an electronic device comprising: a processing unit configured to receive skin temperature data generated by a measuring unit, to receive performance data from a measuring unit, and to determine a theoretical fluid loss value on the basis of the received performance data."

Similarly, clothing that includes sensors have been previously suggested. See, e.g., U.S. Publication No. US2007/0178716 to Glaser et al., which describes a "modular microelectronic-system" designed for use with wearable electronics. U.S. Publication No. US2012/0071039 to Debock et al. describes interconnect and termination methodology fore-textiles that include a "conductive layer that includes conductors includes a terminal and a base separately provided from the terminal. The terminal has a mating end and a mounting end." U.S. Publication No. US2005/0029680 to Jung et al. describes a method and apparatus for the integration of electronics in textiles.

For example, cardiovascular and other health-related problems, including respiratory problems may be detected by monitoring a patient. Monitoring may allow early and effective intervention, and medical assistance may be obtained based on monitored physiological characteristics before a particular health issue becomes fatal. Unfortunately, most currently available cardiovascular and other types of health monitoring systems are cumbersome and inconvenient (e.g., impractical for everyday use) and in particular, are difficult or impractical to use for long-term monitoring, particularly in an unobtrusive manner.

It has been proposed that patient health parameters, including vital signs (such as ECG, respiration, blood oxygenation, heart rate, etc.) could be actively monitoring using one or more wearable monitors, however, to date such monitors have proven difficult to use and relatively inaccurate. Ideally such monitors could be unobtrusively worn by the subject (e.g., as part of a garment, jewelry, or the like). Although such garments have been proposed, see, e.g., U.S. Publication No. 2012/0136231, these garments suffer from a number of deficits, including being uncomfortable, difficult to use, and providing inaccurate results. For example, in applications such as U.S. Publication No. 2012/0136231, a number of individual electrodes are positioned on the garment and connected to a processor by woven conductive fibers or the like; although such garments "require . . . consistent and firm conductive contact with the subject's skin," in order to provide accurate readings, such designs require that the garment be restrictive in order to prevent movement of the garment (and thus sensors) contacting these skin regions. Such a configuration rapidly becomes uncomfortable, particularly in a garment that would ideally be worn for many hours or even days. In addition, even such tightly worn garments often move relative to the wearer (e.g., slip or ride up). Further, devices/garments such as those described in the prior art are difficult and expensive to manufacture, and are often rather "fragile", preventing robust usage and washing. Finally, such devices/garments typically do not allow processing of manual user input directly on the garment, but either relay entirely on passive monitoring, or require an interface of some sort (including off-garment interfaces).

The use of garments including one or more sensors that may sense biometric data have not found widespread use. In part, this may be because such garments may be limited in the kinds and versatility of the inputs that they accept, as well as limits in the comfort, and form factor of the garment. For example, sensors, and the leads providing power to and receiving signals from the sensors have not been fully integrated with the garment in a way that allows the garment to be flexible, attractive, practical, and above all, comfortable. For example, most such proposed garments have not been sufficiently stretchable. Finally, such proposed garments are also limited in the kind of data that they can receive, and how they process the received information.

Thus, existing garments (e.g., devices and wearable sensing apparatuses) and processes for analyzing and communicating the physical and emotional status of an individual may be inaccurate, inadequate, limited in scope, unpleasant, and/or cumbersome.

It is beneficial to have wearable garments having one more sensors that may be comfortably worn, yet provide relatively accurate and movement-insensitive measurements over a sustained period of time.

The sensors integrated with the wearable garments, e.g., sensors implemented with MEMS technology, are generally affected by some noises that limit their performances. For most MEMS devices white noise (random walk noise) and uncorrected bias errors are the main sources of inaccuracy in their measurements. Specifically, white noise (random walk noise) and uncorrected bias errors are the main sources of inaccuracy in the integration of their measurements. Therefore, the sensors integrated with the wearable garments have to be calibrated for accurate measurements.

In addition, in the field of wearable garments, the issues of inaccuracy in measurements are enhanced by the presence of multiple non-rigidly connected sensors. Furthermore, the requirement to keep the garment integrated smartphone away from the sensors because it changes the magnetic environment adds more difficulty to the calibration process. All these requirements complicated the calibration process.

Conventionally, the calibration routine is based on a sequential calibration of each sensor. During this routine, the user has to manually interact with each sensor in order to obtain the calibration parameters. This conventional process can be very long for a wearable garment with several sensors.

There is a need to develop a calibration box for the wearable garment that is able to calibrate the multiple sensors on the wearable garment simultaneously and address the specific challenges of the calibration process for garment integrated sensors.

SUMMARY OF THE DISCLOSURE

A calibration packaging apparatus for storing and calibrating a physiological monitoring garment having a plurality of spatial sensors is herein disclosed. In general, these apparatuses can comprise an inner region for storage; a cover configured to cover the inner region; and a first chamber in the inner region configured to hold a first physiological monitoring garment so that a plurality of position sensors, motion sensors, or position and motion sensors in the garment are secured within the apparatus and free from external electromagnetic interference.

In addition, these apparatuses can include a second chamber or region in (or connected to) the inner region that is configured to hold a phone module; this second region or chamber may be electromagnetically shielded or protected from the chamber or region holding the garment with the sensors, and there may be a connector and/or pass-through region allowing the phone (phone module) to connect to the garment. For example, a separator, which may be loose or attached to the wall(s) of the inner region, may include shielding. The separator may be a sheet, panel, wall, or the like, and may include an opening or pass-through. In some variations the phone may control the calibration, e.g., by connecting to a sensory management system (SMS) on the garment through the separator. In some embodiments, the separator is positioned or positionable in the inner region between the phone module and the garment. The separator is configured to shield magnetic energy between a phone (e.g., phone module) and the garment.

In general, these apparatuses also keep the garments securely stored, and may be useful for shipping, storing and/or packing the garments. These apparatuses may be used to package the garments for sale and/or transmitting to customers; in addition, they may be used longer-term to calibrate the garments (sensors) prior to first and regular use (e.g., daily, weekly, monthly, etc.). Thus, these apparatuses may be configured for stacking and/or for shipping, but may also be optimized for calibrating by a user, including marking and guiding the user for operation. Various configurations useful for both storage and user (e.g., end-user) calibration using the apparatus/packaging are described herein but may include surface markings and treatments, outputs (e.g., LEDs, transparent covers/regions, piezos, etc.) and the like. Gripping regions may be marked or treated for gripping by hand; in some variations, handles may be included. Because the apparatus may be used to store and/or include a phone (e.g., phone module, communications module, telecommunications module, wireless module, etc., including any wireless telecommunications device not limited to smartphones), the apparatus may also generally include one or more ports and/or plugs and/or connectors for connecting to a phone, including power connectors and/or ports. For example, an apparatus (packaging/container) as described herein may include an integrated power connector and/or charger for connecting a phone within the apparatus to wall power.

In order to keep constant the relative distances of a garment's integrated sensors when the garment is secured within the apparatus, the apparatus may include a securement, such as a fixing retainer (e.g., straps, etc.) in the inner region configured to keep all sensors in fixed position relative to the apparatus. Thus, when the apparatus is being rotated or moved during a calibration process, the relative distances between the sensors will be kept constant, which may aid in accurate calibration. In some embodiments, the securement (e.g., retainer) comprises one or more ties. In some other embodiments, the fixing retainer comprises one or more binders. The fixing retainer can include any mechanical components that can be used to keep the objects in fixed relative position and keep constant the relative distances between the objects. The fixing retainer can include ties, binders, brackets, tapes, straps, flanges, strings, ropes, buttons, belts and/or any other things that can keep secure the garment (or at least the sensors on the garment) in place so that the spacing between the sensors being calibrated is kept constant during motion (and calibration) of the apparatus. The fixing retainer can be configured to keep a group of objects together, therefore keep constant the relative distances between the objects.

The apparatus can further comprise at least a marking on the cover, the marking configured to indicate a specific position. In some embodiments, the apparatus can comprise a plurality of markings. The markings can include indications of specific rotation angles, indications of moving directions, indications of angular lines, or the like. The markings can be disposed on at least one of the front cover and/or the bottom cover. In some embodiments, the markings can be disposed on both the front cover and the bottom cover. The markings may be at at, around or near (e.g., within 1, 2, 3 inches of) the outer edge(s) of the housing forming the apparatus. For example, the housing may include a pair of markings that are separated by 90 degrees, and may be used to judge rotation of the housing; equivalent/corresponding markings may be on both top and bottom surfaces, as the user may flip the apparatus during calibration. During a calibration process, the user can rotate and move the apparatus as directed from the instruction.

In general, the apparatus can be made (e.g., entirely made) of non-ferromagnetic and non-diamagnetic materials. It may be particularly helpful to shield magnetic energy from the sensors integrated with the garment during calibration, thus the entire apparatus can be made of non-ferromagnetic and non-diamagnetic materials (e.g., non-magnetic materials). In some other embodiments, the chamber holding the monitoring garment with integrated sensors can be made of non-ferromagnetic and non-diamagnetic materials, and/or shielded from exogenous magnetic fields. For example, the apparatus can be made of thermoformed carton box in one embodiment. The apparatus can be made of molded plastic in another embodiment.

In some embodiments, the apparatus can further comprise an ergonomic hand-grip which can be grabbed by the user easily and comfortable. The ergonomic hand-grip can further facilitate smooth rotation in all directions during the calibration process. In some embodiments, the hand-grip can be made of rubber. In some other embodiments, the hand-grip can be made of soft-touch plastic.

The apparatus can comprise a cover and a bottom surface. The bottom surface can be configured to slide open for calibration process. In some embodiments, the apparatus can be in a cylindrical shape with a circular cross section. The circular shape can be easily manipulated to facilitate smooth rotation in all directions. The diameter of the circular cross-section can be between about 10 cm to about 50 cm. The height of the apparatus can be substantially less than the diameter of the cross section. In some embodiments, the height of the apparatus can be from about 1 cm to about 10 cm. In some other embodiments, the cross section of apparatus can have an oval shape, an elliptical shape, a rectangular shape, a square shape or any other shape. The apparatus may be configured to open in a clamshell-like fashion (and/or may be clamshell shaped) or it may be configured have a removable cover/top.

In some embodiments, calibration can be automatically performed by the phone module. The processor of the phone module can be programmed to perform automatic calibration computation. The user can be prompted to initiate a calibration process by a user friendly interface. The user can set up the calibration process through the smart screen of the phone module. The smart screen of the phone module can further provide quick and easy feedback of calibration status by showing a progress bar. In some embodiments, the phone module can provide feedback of calibration status by a blinking RGB LED.

In some other embodiments, the calibration packaging apparatus can further comprise a controller in the inner region. The controller can be connected with the sensory management system of the garment. The controller can be configured to perform automated calibration parameter computation. The user can be prompted to initiate a calibration process by a user friendly interface of the controller. The user can set up the calibration process through the user interface. The calibration packaging apparatus can further comprise an output in the inner region. The output can provide feedback of calibration status, e.g., by showing a progress bar or a blinking RGB LED.

In general, the calibration packaging apparatus can be configured to be connected to a remote processor (e.g., a cloud processor) through the phone. The apparatus can be further configured to be a docking station.

In general, the calibration packaging apparatus can further comprise additional chambers configured to hold all the accessories for the physiological monitoring garment, such as an earphone, an earphone cable, a wristband, a camera, a charger cable, a USB adapter and a USB cable. The various chambers may include openings sized to permit passage of the connectors so that the various garment(s) or portions of the garments may be stored in the apparatus in a connected configuration, allowing coordinated/simultaneous calibration of sensors in all of the garment portions. In some embodiments, the apparatus can be configured to have multiple levels such that the components can be stacked on top of the other components. In this way, the apparatus can be compact, so that it can easily fit into a suitcase and be easily transported in a suitcase.

In general, a calibration packaging apparatus for a physiological monitoring garment can comprise an inner region for storage; a cover configured to cover the inner region; a first physiological monitoring garment comprising a first plurality of position sensors, motion sensors, or position and motion sensors; and a first chamber in the inner region configured to hold the first physiological monitoring garment. The apparatus can further comprise a phone module; a second chamber in the inner region configured to hold the phone module. The apparatus can be configured to have a connector within the first chamber configured to connect to a sensory management system on the garment with an output in another chamber of the inner region or through the cover. The apparatus can comprise a fixing retainer in the inner region configured to keep constant a plurality of relative distances between the first plurality of position sensors, motion sensors, or position and motion sensors during a calibration process. The apparatus can comprise a plurality of markings to indicate positions to guide the user to rotate or move the apparatus during the calibration process.

In some embodiments, the apparatus can further comprise a separator in the inner region between the phone module and the garment. The separator is configured to shield magnetic energy between the phone module and the garment. The separator can be made of non-ferromagnetic and non-diamagnetic materials.

In some embodiment, the phone module is configured to perform automatic calibration parameter computation and provide feedback of the calibration process. In some other embodiments, a controller embedded with the apparatus is configured to perform automatic calibration parameter computation and an output embedded with the apparatus is configured to provide feedback of the calibration process.

In some embodiments, the apparatus can further comprise another chamber configured to hold a second physiological monitoring garment. The second physiological monitoring garment can comprise a second plurality of position sensors, motion sensors, or position and motion sensors. The first garment can be configured to be connected with the second garment during the calibration process such that the first plurality and the second plurality of position sensors, motion sensors, or position and motion sensors are calibrated at the same time.

Also described herein are methods of using any of these apparatuses to calibrate a plurality of sensors on a garment, such as any of the garments described in U.S. patent application Ser. No. 14/023,830, filed on Sep. 11, 2013, titled "WEARABLE COMMUNICATION PLATFORM;" U.S. patent application Ser. No. 14/331,185, filed on Jul. 14, 2014, titled "METHODS OF MAKING GARMENTS HAVING STRETCHABLE AND CONDUCTIVE INK;" U.S. patent application Ser. No. 14/331,142, filed on Jul. 14, 2014, titled "COMPRESSION GARMENTS HAVING STRETCHABLE AND CONDUCTIVE INK;" U.S. Provisional Patent Application No. 61/699,440, filed Sep. 11, 2012, titled "SMARTWEAR SYSTEM;" U.S. Provisional Patent Application No. 61/862,936, filed on Aug. 6, 2013, titled "WEARABLE COMMUNICATION PLATFORM;" and U.S. Provisional Patent Application No. 61/950,782, filed on Mar. 10, 2014, titled "PHYSIOLOGICAL MONITORING GARMENTS."

In general, a method of calibrating a physiological monitoring garment may include placing the garment within the calibration packaging apparatus; connecting a sensory management system (SMS) on the garment with a phone (e.g., phone module) or a control system (e.g., remote processor) and/or a cloud-based remote processor, and guiding the user through a series of movements and static positions to calibrate a plurality of sensor types during a calibration process.

For example, disclosed herein is a method of calibrating a physiological monitoring garment. The method can comprise placing a first physiological monitoring garment inside a first chamber in an inner region of a calibration packaging apparatus. The garment can comprise a first plurality of position sensors, motion sensors, or position and motion sensors. The method can further comprise connecting a sensory management system on the garment with an output in another chamber of the inner region or through a cover and using a fixing retainer in the inner region to keep constant a plurality of relative distances between the first plurality of position sensors, motion sensors, or position and motion sensors during a calibration process. In some embodiments, the method further comprises using a separator in the inner region between the phone module and the garment, to shield magnetic energy between the phone module and the garment.

The method can further comprise initiating a calibration process, moving and rotating the apparatus following an instruction; allowing all sensors to be calibrated simultaneously; and monitoring the calibration process by a feedback signal.

In some embodiments, the method can comprise initiating a calibration process through a smart screen of the phone module. In some other embodiments, the method can comprise initiating a calibration process through a controller in the inner region of the apparatus. In some embodiments, the method can comprise allowing all sensors to be calibrated simultaneously the phone module. In some other embodiments, the method can comprise allowing all sensors to be calibrated simultaneously by a controller in the inner region of the apparatus.

A method of allowing calibration of a physiological monitoring garment is disclosed. The method can comprise a first physiological monitoring garment inside a first chamber in an inner region of a calibration packaging apparatus, and the garment comprising a first plurality of position sensors, motion sensors, or position and motion sensors. The method further comprise connecting a sensory management system on the garment with an output in another chamber of the inner region or through a cover; using a fixing retainer in the inner region to keep constant a plurality of relative distances between the first plurality of position sensors, motion sensors, or position and motion sensors during a calibration process; and using a separator in the inner region between the phone module and the garment to shield magnetic energy between the phone module and the garment. The method can comprise allowing a calibration process to be initiated; showing an instruction to move and rotate the apparatus on the smart screen; allowing the apparatus to be moved and rotated following the instruction; calibrating all sensors to be calibrated simultaneously; providing feedback of the calibration process; and indicating completion of the calibration process.

BRIEF DESCRIPTION OF THE DRAWINGS

FIGS. 3A-3C schematically illustrate another embodiment of the calibration packaging apparatus, where the apparatus is made of molded plastic.

FIGS. 4A and 4B schematically illustrate a wearable garment placed inside a calibration packaging apparatus while all the sensors integrated with the garment can be calibrated simultaneously.

FIG. 8C schematically illustrate a top view of a multi-level calibration packaging apparatus.

FIGS. 12A and 12B illustrate a stand, and a stand holding an example of a calibration box, respectively, as described herein.

FIG. 13A shows an aperture or window through an exemplary calibration box.

FIGS. 13B, 13C and 13D show front, side and top views, respectively, of a phone module attached to a garment through an aperture such as the aperture shown in FIG. 13A.

FIG. 15A shows an external view, while FIG. 15B shows a view of the inside of the calibration box with the box made transparent.

DETAILED DESCRIPTION

The present invention will be described in detail with reference to the accompanying figures. This invention may be embodied in many different forms and should not be construed as limited to the example embodiments discussed herein.

In general, described herein are apparatuses (systems and devices) for calibration of garments having multiple sensors, including (but not limited to) integrated sensors for sensing: movement, temperature, electrical signals, touch (e.g., contact), acceleration, magnetic fields, etc. These garments may be referred to as wearable physiological monitoring garments. For example, a garment may include an integrated attitude heading reference system (e.g., accelerometer, gyroscope, magnetometer, etc.). These garments may also include a sensor management system (SMS), and in some variations the garment may include or be configured to work with, a communications subsystem (also referred to herein as a phone module, PM, or communication module). The communications subsystem typically includes a power supply, connectivity circuitry and controller for communicating wirelessly, e.g., by WiFi, mobile broadband, Bluetooth, etc., with one or more remote processors. A communications subsystem may include computational capabilities (e.g., may include memory and one or more processors). The communications subsystem (phone module) may be a separate component having its own housing, or it may be integrated into the garment and/or configured to couple to the garment. In some variations the communications subsystem is a smartphone, including a general-purpose smartphone that is adapted to communicate with the garment (including the SMS).

The apparatuses described herein may generally operate as both garment storage containers (holding the sensor-containing garment(s)) and calibration devices, that may prepare, e.g., by calibrating, the plurality of sensors on the device for operation. These apparatuses may hold the one or more garments, and the plurality of sensors integrated into the garment, stable during a calibration procedure. The apparatus (e.g., calibration container) is configured such that the sensors are held at a fixed position relative to each other; these positions may be known to the controller directing the calibration. The portion of the apparatus directing the calibration may be one or more of: the SMS on/in the garment, the phone module/communications subsystem on/in the garment or separate from the garment, a control system (e.g., phone, laptop, etc.) in communication with the garment and/or a remote server (e.g., cloud-based server). This may allow the sensors to be calibrated for the entire garment and/or any associated garments, effectively.

Figure 1A:
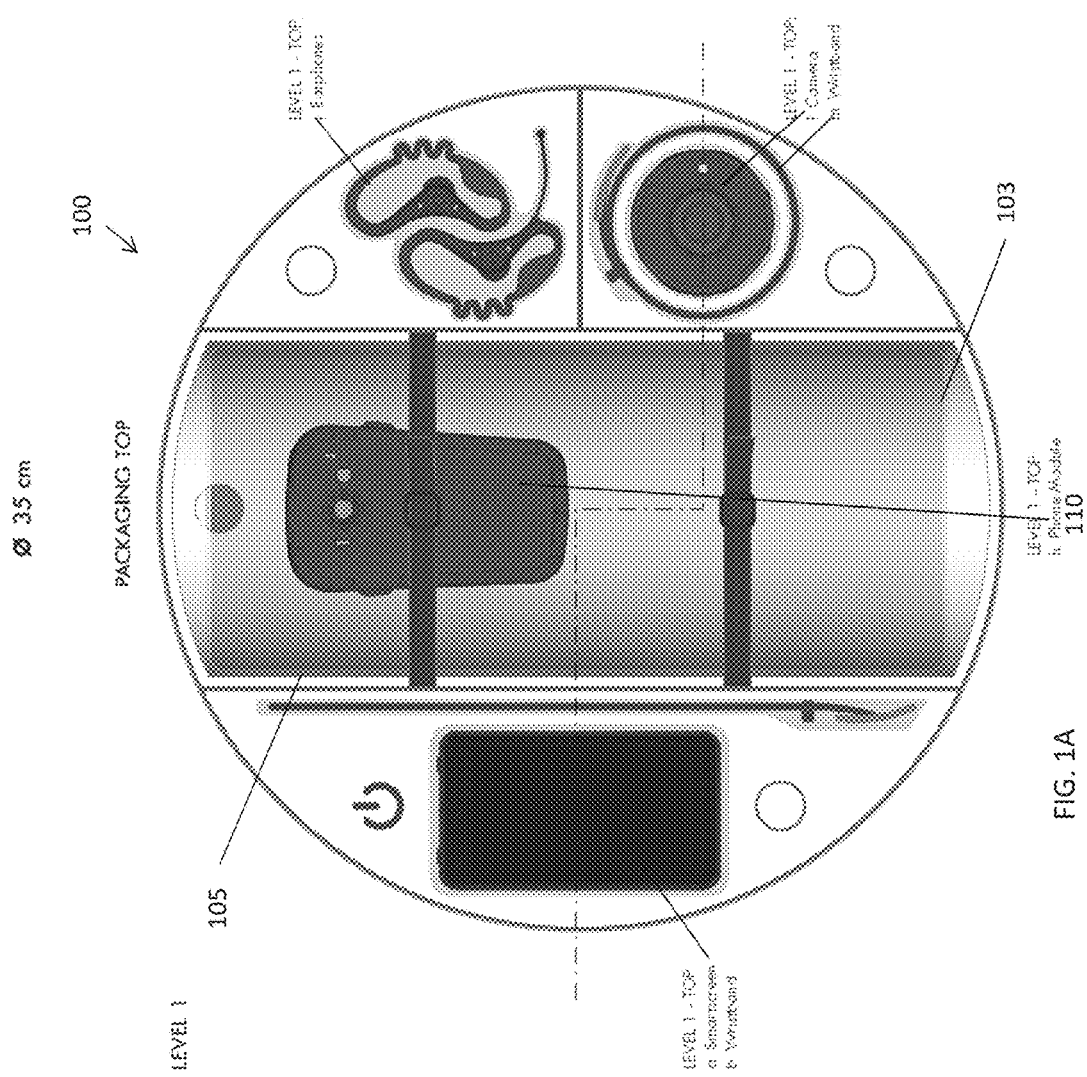
FIG. 1A schematically illustrates a top view of a calibration packaging apparatus for a wearable physiological monitoring garment with cover removed.
Figure 1B:
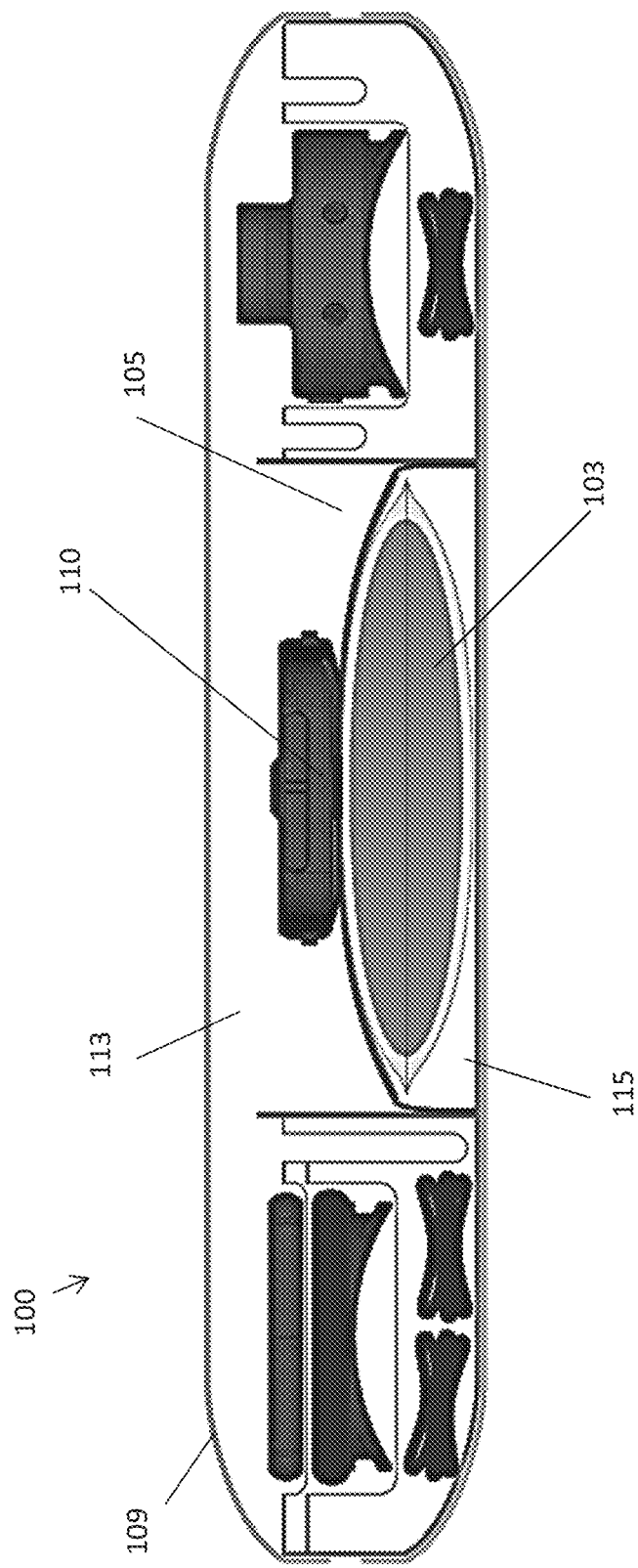
FIG. 1B schematically illustrates a section view of a calibration packaging apparatus for a wearable physiological monitoring garment.

FIG. 1A schematically illustrates a top view of one example of a calibration packaging apparatus 100 for a wearable physiological monitoring garment 103 with a top cover of the apparatus removed. FIG. 1B schematically illustrates a section view of the same calibration packaging apparatus for a wearable physiological monitoring garment. In this example, the packaging apparatus comprises an inner region 105 for storage, a cover 109 configured to cover the inner region, a chamber in the inner region 111 configured to hold a physiological monitoring garment and another chamber 113 to hold a phone module. The physiological monitoring garment 103 can comprise various position sensors, motion sensors, or position and motion sensors. The garment can further comprise a sensory management system which can be configured to connect to and manage the various sensors on the garment. In some variations the apparatus can include a connector within the chamber holding the garment. The connector can be configured to connect to a sensory management system on the garment and provide a connection to a controller in or on the apparatus; in some variations the connector is configured to hold and integrate with a phone (e.g. smartphone); the phone 110 may be held in the separate chamber 113 of the inner region 105 of the apparatus. In some embodiments, the output of the connector can be in another chamber of the inner region. In some other embodiments, the output can be connected through a hole in the cover. Alternatively or additionally, the phone may be directly connected to the garment (e.g., the SMS on the garment), for example, through a hole in a separator between the first chamber 111 and the second chamber 113.

For different position sensors and motion sensors in the one or more garments (wearable physiological monitoring garments) to be stored and calibrated using these apparatuses, the related calibration methods can be different. For example, for gyroscope-based sensors, generally, the factory-performed calibrations may be sufficient to compensate the sensitivity scale factor, but may be affected by a constant bias error. The constant bias error can be estimated by taking a simple calibration in which the bias is computed as a long-term average of the sensor output while the sensor is in a stationary condition. The constant bias error can be compensated by simply subtracting the bias from the output. Alternatively, in some variations the apparatuses described herein may be configured to calibrate the sensitive scale factor of the gyroscope-based sensors.

For accelerometer based sensors, generally, the factory-performed calibrations may be sufficient to compensate the sensitivity scale factor, but could be affected by a constant bias error. The bias calibration of the accelerometer may be complicated by gravity, since a component of gravity acting on the accelerometer may appear as a bias. It may therefore be helpful to know the precise orientation of the device with respect to the gravitational field to measure the bias. The constant bias error may be compensated by simply subtracting the bias from the output. Alternatively, in some variations the apparatuses described herein may be configured to calibrate the sensitive scale factor of the accelerometer sensors.

For magnetometer based sensors, calibration may be important. The magnetometer calibration may be based on the fact that the earth's magnetic field vector can be assumed to be constant when measured from any orientation in the same location. By moving the magnetometer in as many different orientations as possible, while maintaining position limited in strict area and logging the raw data, it may be possible to plot the points in a three dimensional space. Ideally, this cloud of points may show a perfect sphere of unit radius and center in the origin.
Nevertheless, before the calibration, the points' distribution may not represent a prefect sphere, but generally, may have an ellipsoid form. Therefore, the magnetometer based sensors may be calibrated to have a perfect sphere of unit radius and center in the origin.

In any of the variations described herein, the packaging apparatus may include a wearable garment having a variety of sensors, including those described above. In order to perform calibration for various types of sensors, the calibration box for the wearable garment can be configured to keep constant the relative distances between various sensors during the calibration process, enable the sensors to move in different directions during the calibration process and ensure an appropriate distance between the garment integrated smartphone and the sensors in order to shield magnetic energy.

In general, the apparatuses described herein may also be configured to allow concurrent calibration of all of the sensors in the one or more garments, including sequentially concurrent calibration (calibrating different sets or types of sensors together, where each different type or set is calibrated sequentially) and/or simultaneous concurrent calibration.

As shown in FIGS. 1A and 1B, the packaging apparatus for the wearable garment can be used as the calibration box. In this way, the packaging becomes an reusable apparatus for use with a wearable device and its parts and accessories. The packaging apparatus can be cost effective (low cost of production, storage, and transportation) and ensure protection of devices and its parts. By using the packaging for the product as the calibration box, not only the cost can be reduced, but also the calibration process can be facilitated and streamlined. Any of these apparatuses may also include control logic (software, firmware, and/or hardware) guiding operation of the calibration, including instructing the user to manipulate the packaging/calibration box portion of the apparatus. In some variations the apparatus includes application software that runs on a processor associated with the garment being calibrated, such as a smartphone that communicates with the garment; the application software ("app") may coordinate the calibration, including initiating calibration of each of the different sets of sensors, placing the sensors in a calibration state, instructing the user to manipulate the portion of the apparatus holding the garment(s) (e.g., the calibration box), calculating any calibration offsets and/or correction factors (or relationships), storing any calibration offsets and/or correction factors (or relationships), and/or transmitting any calibration offsets and/or correction factors (or relationships) to the garment (e.g., SMS, controller, etc.) and any remote processors. In addition to calibrating the one or more sensors in/on the garment, the apparatus may initialize the electronics components (e.g., clear memories, initialize communications protocols) and/or run diagnostics on the sensors and any control subsystems, as well as install any updates/edits to the software or firmware on the garment or any of its subsystems.

In some embodiments, the calibration apparatus (e.g., the calibration box portion of the apparatus) may be generally disc-shaped, or have a flattened polygonal shape (e.g. with a plurality of flat sides, including a cylinder having a rectangular-shaped cross-section, a triangular-shape cross-section, a pentagonal-shaped cross-section, a hexagonal-shaped cross-section, a heptagonal-shaped cross-section, an octagonal-shaped cross-section, etc.), and may have a flattened overall appearance, and may include flat bottom, flat top and/or flat bottom and top surfaces. The top and/or bottom surfaces may be configured to slide open such that the user can access the inner region of the apparatus and closed before initiating the calibration process. In some other embodiments, the user can open and close the cover of the apparatus and thereafter initiate the calibration process.

Figure 2A:
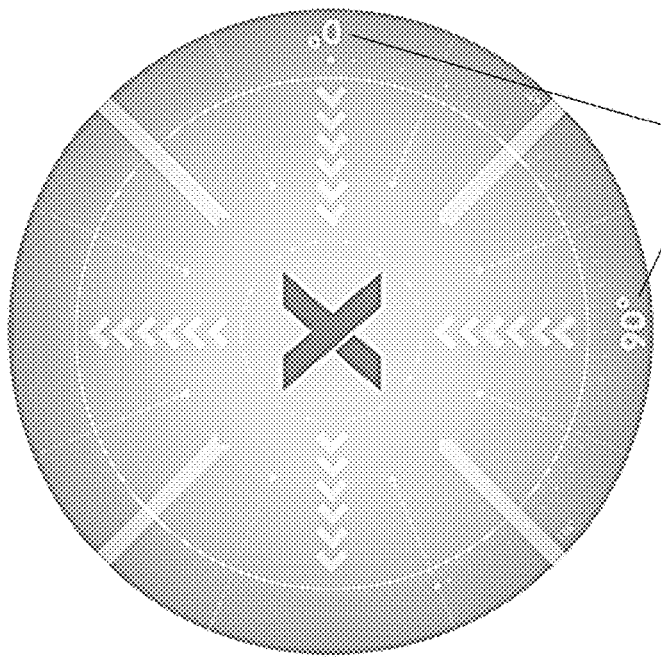
FIG. 2A schematically illustrates a top view of a top cover of the calibration packaging apparatus.
Figure 2B:
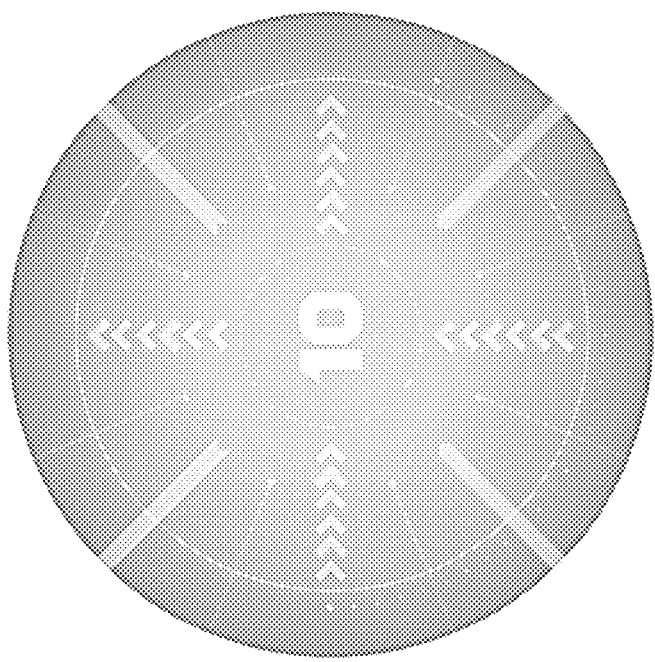
FIG. 2B schematically illustrates a bottom view of a bottom cover of the calibration packaging apparatus.
Figure 2C:
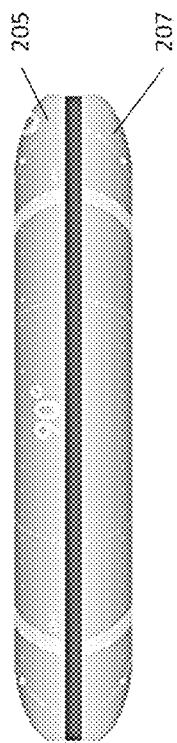
FIG. 2C schematically illustrates a side view of the calibration packaging apparatus.

FIGS. 2A-2C schematically illustrate a top, bottom and side views, respectively of one example of a calibration packaging apparatus. As shown in FIGS. 2A-2C, the apparatus can further comprise at least one marking to indicate the specific position. In some embodiments, the apparatus can comprise a plurality of markings 203. The markings can include indications of specific angles (e.g., around the perimeter region of the top/bottom/sides), indications of moving directions, indications of angular lines, etc. The markings can be disposed on at least one of the front cover 205 and the bottom cover 207, and/or sides of the apparatus. In some variations the top region may be removable (as a cover 205) and/or the bottom may be removable as a cover 207; the top and bottom may be separable or connected (e.g., via a hinge, etc.). In some embodiments, the markings can be disposed on both the front cover and the bottom cover.

During a calibration process, the user can rotate and move the apparatus as directed from the instructions, and described in greater detail below.

As seen in FIGS. 2A-2C, the apparatus can have ergonomic form factor which allow easy manipulation of the calibration box to facilitate rotation. Specifically, for magnetometer based sensors, smooth rotation in all directions is most helpful. The apparatus can further have a soft-touch and easy-to-grab edge such that the user can easily rotate the apparatus in any direction.

In some embodiments, the apparatus can be in a cylindrical shape with a circular cross section. The circular shape can be easily manipulated to facilitate smooth rotation in all directions. The diameter of the circular cross-section may be between about 10 cm to about 50 cm. The height of the apparatus can be substantially less than the diameter of the cross section. In some embodiments, the height of the apparatus can be from about 1 cm to about 10 cm. In some other embodiments, the cross section of apparatus can have an oval shape, an elliptical shape, or a polygonal shape (e.g., a rectangular shape, a triangular shape, a hexagonal shape, a square shape, etc.) or any other shape as mentioned above.

The apparatus may shield magnetic energy from the sensors integrated with the garment, which may help achieve accurate calibration. In some embodiments, the entire apparatus can be made of non-ferromagnetic and/or non-diamagnetic materials. In some other embodiments, the chamber holding the monitoring garment with integrated sensors can be made of non-ferromagnetic and/or non-diamagnetic materials. In some alternative embodiments, the apparatus can further comprise a shield made of non-ferromagnetic and/or non-diamagnetic materials and the shield is configured to cover the garment. In some other embodiments, the apparatus can further comprise a shield made of non-ferromagnetic and/or non-diamagnetic materials and the shield is configured to cover the entire apparatus. For example, the apparatus can be made of thermoformed carton box in one embodiment as shown in FIGS. 2A-2C.

FIGS. 3A-3C schematically illustrate another embodiment of the calibration packaging apparatus, where the apparatus is made of molded plastic. In some embodiments, the apparatus can further comprise an ergonomic hand-grip 307 which can be grabbed by the user easily and comfortable. The ergonomic hand-grip can further facilitate smooth rotation in all directions. In some embodiments, the hand-grip can be made of rubber. In some other embodiments, the hand-grip can be made of any appropriate soft-touch plastic (including silicones, etc.).

In some embodiments, the top cover and/or the bottom can be transparent 305. A transparent cover can enable the user to easily observe the contents and monitor the calibration status without opening the cover.

FIGS. 4A and 4B schematically illustrate a wearable garment 405 placed inside a calibration packaging apparatus (or a chamber of this portion of the apparatus) while all the sensors integrated with the garment can be calibrated simultaneously. Thus, the calibration packaging apparatus can be configured to be connected to all the sensors integrated with the wearable garment and simultaneously calibrate all the sensors.

In some embodiments, the apparatus may hold (in a single chamber or more than one chambers) more than one garments or garment accessories. For example, an apparatus can have more than one chamber to hold several garments. The chambers may be stacked on top each other, as described in greater detail below. All the garments can be connected during the calibration procedure such that all the sensors in all different garments/garment accessories can be calibrated at the same time. For example, a shirt having sensors may be connected for calibration in the apparatus with a pair of pants/tights for calibration.

Figure 5B:
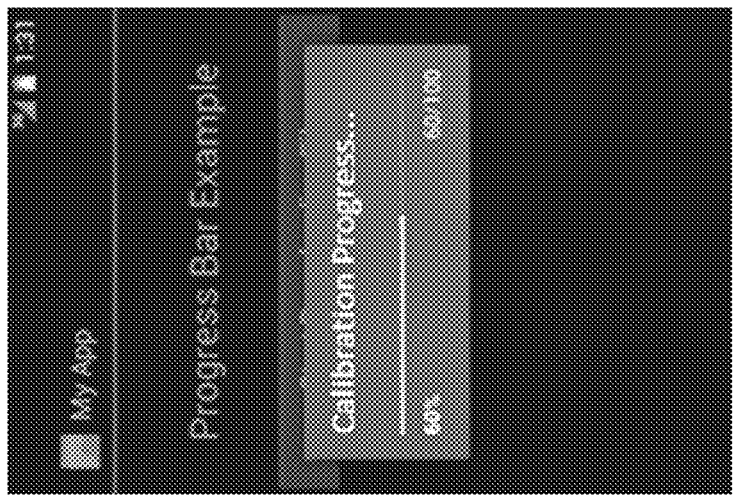
FIGS. 5A and 5B schematically illustrate feedbacks to the user about the calibration progress status.
Figure 5A:
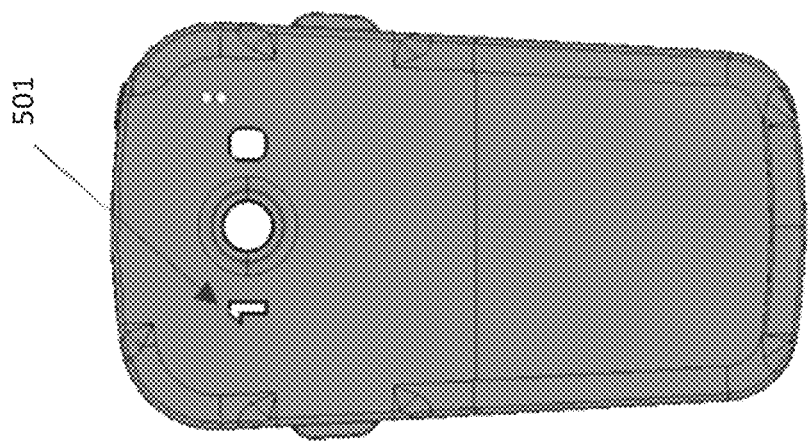

FIGS. 5A and 5B schematically illustrate feedbacks to the user about the calibration progress status. In some embodiments, automated calibration parameter computation performed by a processor (e.g., a phone) connected (e.g., directly connected or wirelessly connected) to the garment. The processor of the phone (phone module) can run software to perform automatic calibration computation. As the processor is controlled by the software (e.g., "app") to step through the calibration of one or more sensors in the garment(s), the user can be prompted to initiate a calibration process by a user-friendly interface (see, e.g., FIG. 5B). The user can set up the calibration process through the smart screen of the phone or to a screen/smart screen (e.g., touchscreen, etc.) connected to the garment, including wearable touchscreen. The screen of the phone module can further provide quick and easy feedback of calibration status by showing an indicator such as a progress bar. In some embodiments, the phone module can provide feedback of calibration status by a blinking RGB LED 501.

The calibration packaging apparatus can be connected to a remote server (e.g., cloud server) through the connectivity of the phone/phone module (4G, Bluetooth, Wi-Fi), which can provide enhanced computational power for the calibration algorithm application. As described the term 'phone' is used throughout here which may include a conventional or dedicated smartphone having wireless communications capability, but in general it may refer to any telecommunications circuitry, including a controller integrated into the apparatus, and handheld phones, or any other wearable device (watch, jewelry, etc.) that may be operated with the garment.

For example, in some other embodiments, the calibration packaging apparatus can further comprise a controller in the inner region. The controller can be connected with the sensory management system (SMS) of the garment. The controller can be configured to perform automated calibration parameter computation. The user can be prompted to initiate a calibration process by a user friendly interface of the controller. The user can set up the calibration process through the user interface. The calibration packaging apparatus can further comprise an output in the inner region. The output can provide feedback of calibration status by showing a progress bar or a blinking RGB LED.

In some embodiments, the calibration packaging can be used as a docking station for electronic components. In some other embodiments, the calibration packaging can be used as a charging station. The calibration packaging (box, etc.) may be the apparatus or a part of the apparatus; the apparatus may also include the control logic (e.g., "app") and/or any communications subsystem (e.g., phone module) and/or a garment including the sensors. In some variations the apparatus is a system including the calibration packaging (e.g., box or container) and the application software that may control the use of the calibration packaging to calibrate the garment.

Figure 6A:
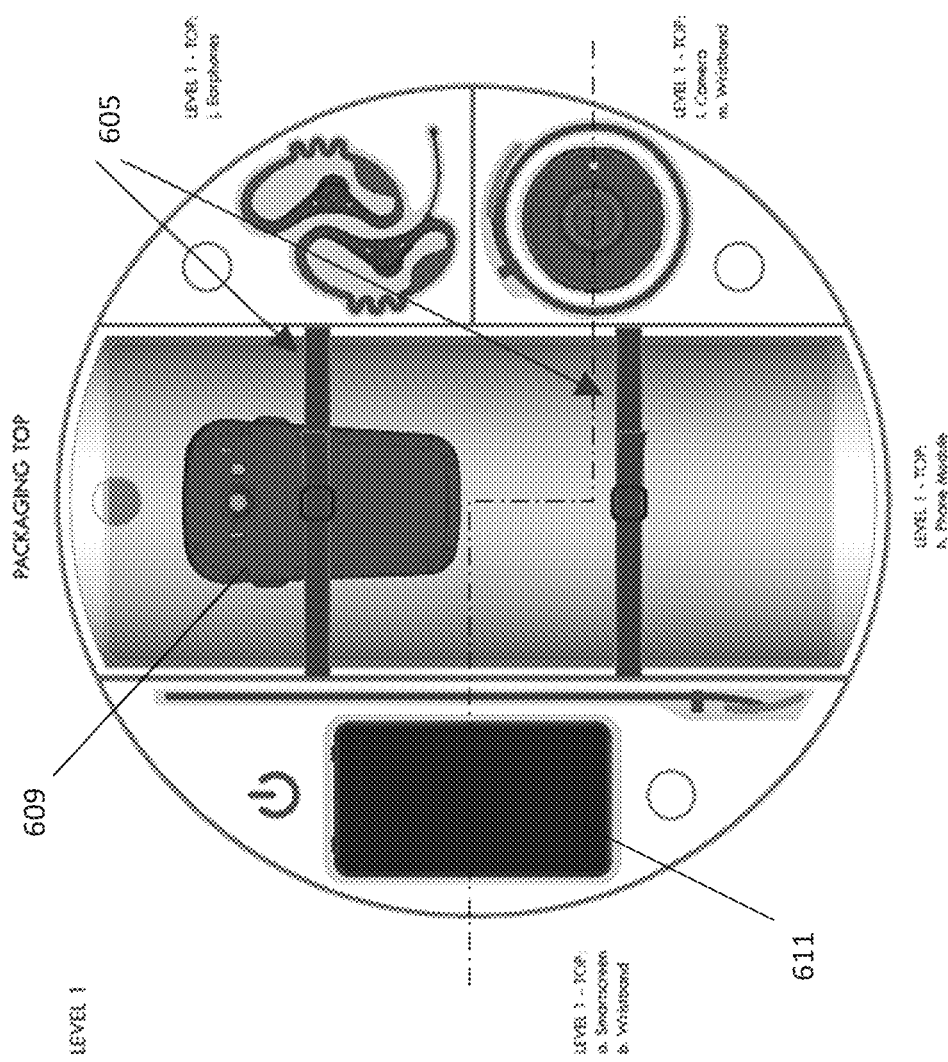
FIG. 6A schematically illustrates a fixing retainer in the inner region of the apparatus configured to keep constant the relative distances between the sensors during a calibration process.

FIG. 6A schematically illustrates a fixing retainer in the inner region of the apparatus configured to keep constant the relative distances between the sensors during a calibration process. In general, the apparatuses described herein may include one or more (e.g., 2, 3, 4, 5, 6, 7, 8, 9, 10, etc.) securements 605 that hold the garment (and in some variations the sensors on the garments directly) in a fixed position within the apparatus. These securements generally hold the garment securely within the apparatus, and may include straps, belts, buckles, snaps, webbing, wires, hooks, straps, elastics, ties, clamps, grips, pouches, etc. The securements may be referred to herein as retainers or fixing retainers, as they retain and/or fix the garment (or a portion of the garment, and specifically a positional sensor) in place relative to the other sensors and/or relative to the apparatus. Thus a securement (e.g., fixing retainer) may include any mechanical components that can be used to keep the sensors in fixed relative position and keep constant the relative distances between the sensors. The fixing retainer can include ties, binders, brackets, tapes, glues, flanges, strings, ropes, buttons, belts, etc. that can keep constant the relative distances between the objects. The fixing retainer can be configured to keep a group of objects together, therefore keep constant the relative distances between the objects. As discussed above, the apparatus may keep constant the relative distances between the sensors during the calibration process in order to compute constant bias error. Moreover, if the sensors were free to move inside the calibration packaging apparatus, undesired collision may happen which can result in magnetic distortions for the garment integrated sensors.

As seen in FIG. 6A, ties or belts 605 can be used to keep the garment (and/or connector for coupling to a phone) in fixed position relative to the calibration packaging apparatus. In some embodiments, two ties or belts may be used. In some other embodiments, one tie or belt can be used. In some other embodiments, multiple ties or belts can be used. In some alternative embodiments, both the apparatus and the garment may have connectors at designated positions such that the garment will move together with the apparatus during the calibration process, therefore, the relative distances of various garment integrated sensors will be kept constant during the calibration process.

Figure 6B:
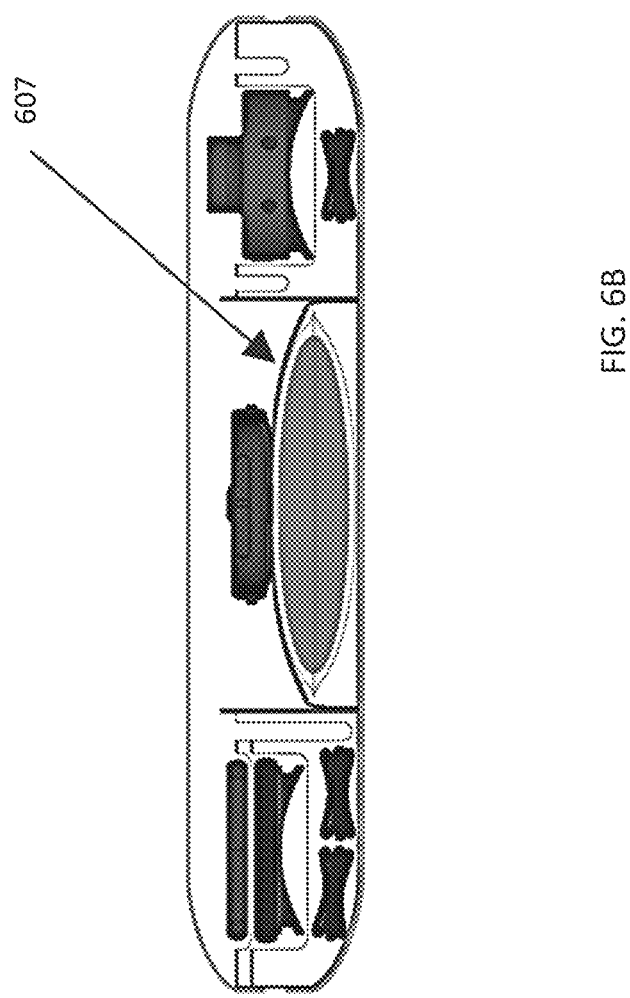
FIG. 6B schematically illustrates a separator which is configured to separate the garment integrated sensors from the phone module.

FIG. 6B schematically illustrates a separator which is configured to separate the garment integrated sensors from the phone module. The phone module (connector 609) or phone 611 can cause magnetic distortions to the sensors integrated with the garment. The calibration packaging apparatus can comprise a separator 607. A separator can be configured to separate the garment having integrated sensors from a phone coupled to the garment (directly or indirectly) in order to shield the magnetic energy emitted by the phone form the sensors. This may help avoid magnetic distortions during calibration. In some embodiments, the separator 607 can be plastic. In some other embodiments, the separator 607 can be formed entirely of non-magnetic materials, and/or may include magnetic shielding. In some embodiments, the separator can be embedded and/or attached in the chamber holding the monitoring garment. In some embodiments, the separator can be configured to enclose the sensory garment. In some embodiments, the separator can be configured to enclose the phone module. In any of these example, the separator may include an opening or passage allowing connection of the phone to the SMS of the garment.

Either or both the separator and/or the calibration chamber/apparatus may be configured to hold or secure the phone at least a minimal distance from the garment (e.g., sensors on the garment), to prevent interference. The minimal distance may be 1 cm, 2 cm, 3 cm, 4 cm, 5 cm, 6 cm, 7 cm, 8 cm, 9 cm, 10 cm, 11 cm, etc.). For example, an apparatus may include a phone securement, securing the phone to the separator or within the inner chamber (in a separate region from the garment). In some variations the separator includes a spacer (which may be electromagnetically shielded) for separating the phone from the garment. A spacer may have a thickness that is equal to or greater than the minimal distance for separating the phone circuitry from the garment, even when the phone is connected (e.g., through the opening in the separator) to the SMS of a garment.

Figure 7A:
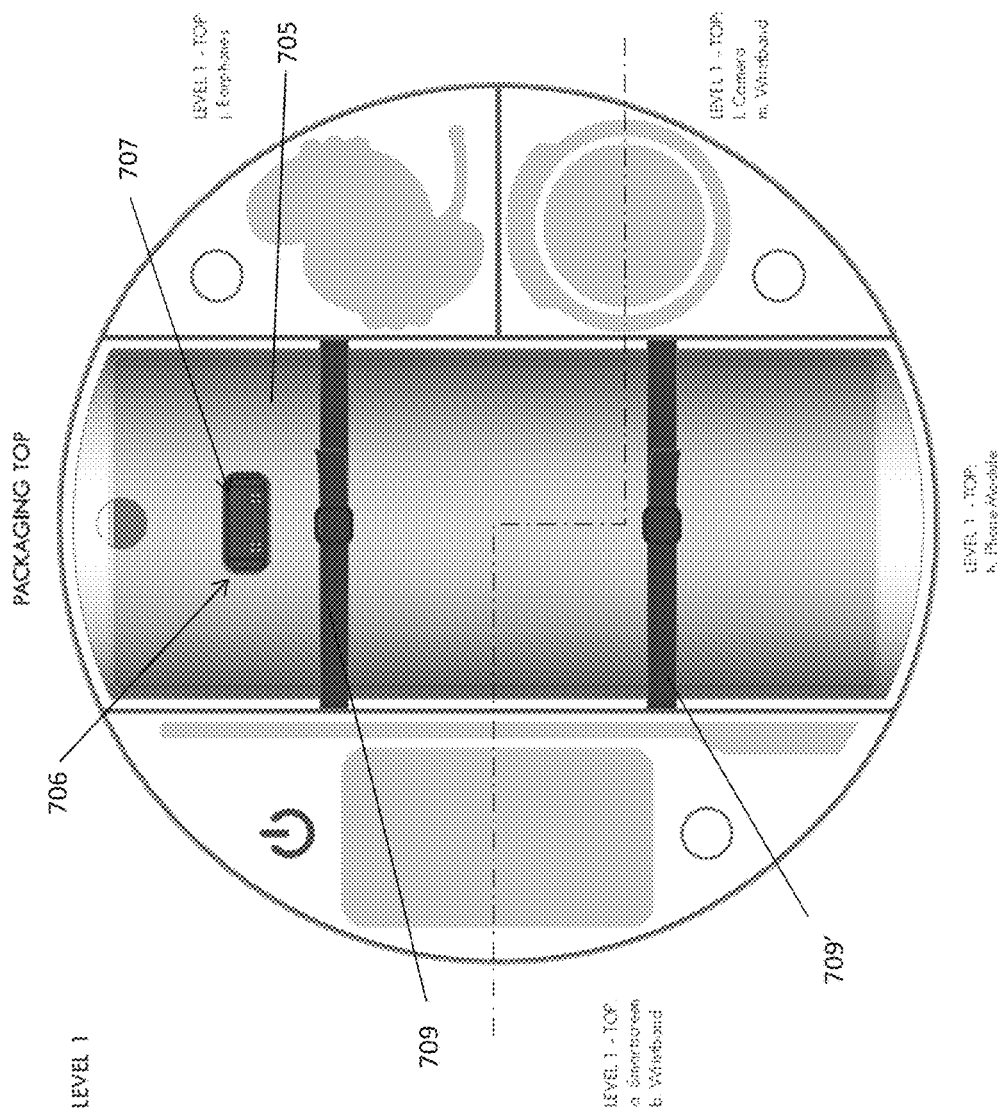
FIG. 7A shows a top view of one example of a calibration packaging apparatus.
Figure 7B:
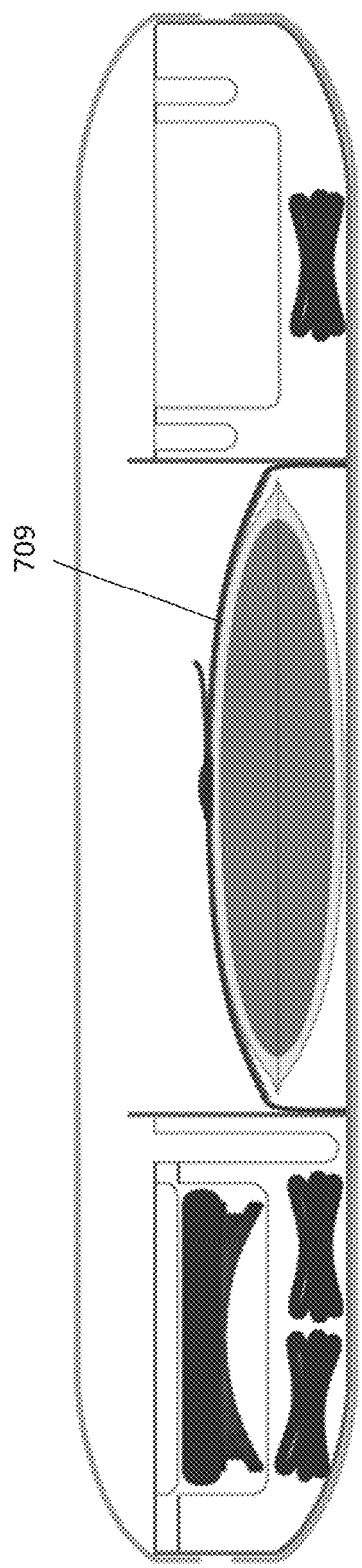
FIG. 7B shows a side view of the calibration packaging apparatus of FIG. 7A.

FIGS. 7A and 7B illustrate another view of an apparatus similar to those shown above, from a top (FIG. 7A) and side sectional (FIG. 7B) views. In FIG. 7A, the view shows a separator 705 having an opening 706 through which the SMS connector 707 is visible. The phone (not shown) may be connected through this opening. Securements (shown as straps 709, 709') may hold the separator over the garment, and may also secure the garment in place. The straps may be elastic, and in this configuration secure over the separator, rather than directly against the garment. This may prevent/reduce wrinkling, while still securing the sensors relative to each other and/or the apparatus.

Figure 8B:
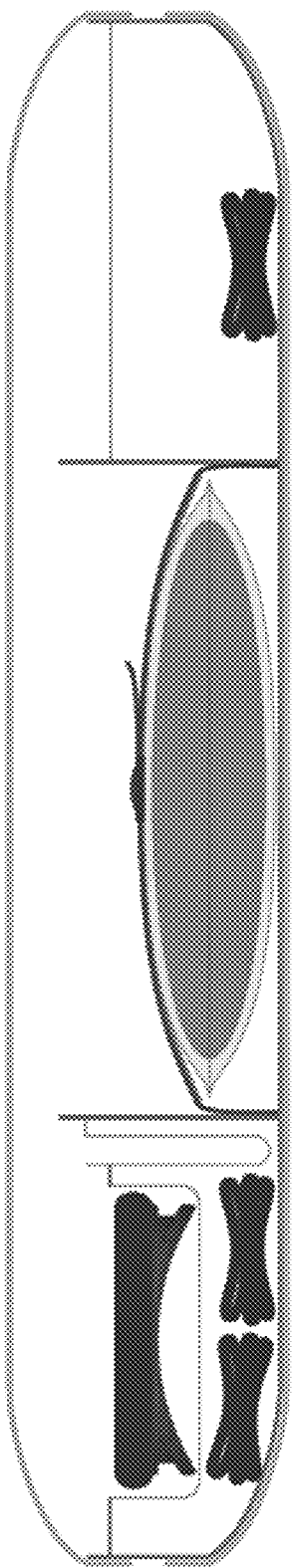
FIG. 8B schematically illustrate a side view of the calibration packaging apparatus with additional chambers shown in FIG. 8A.
Figure 8A:
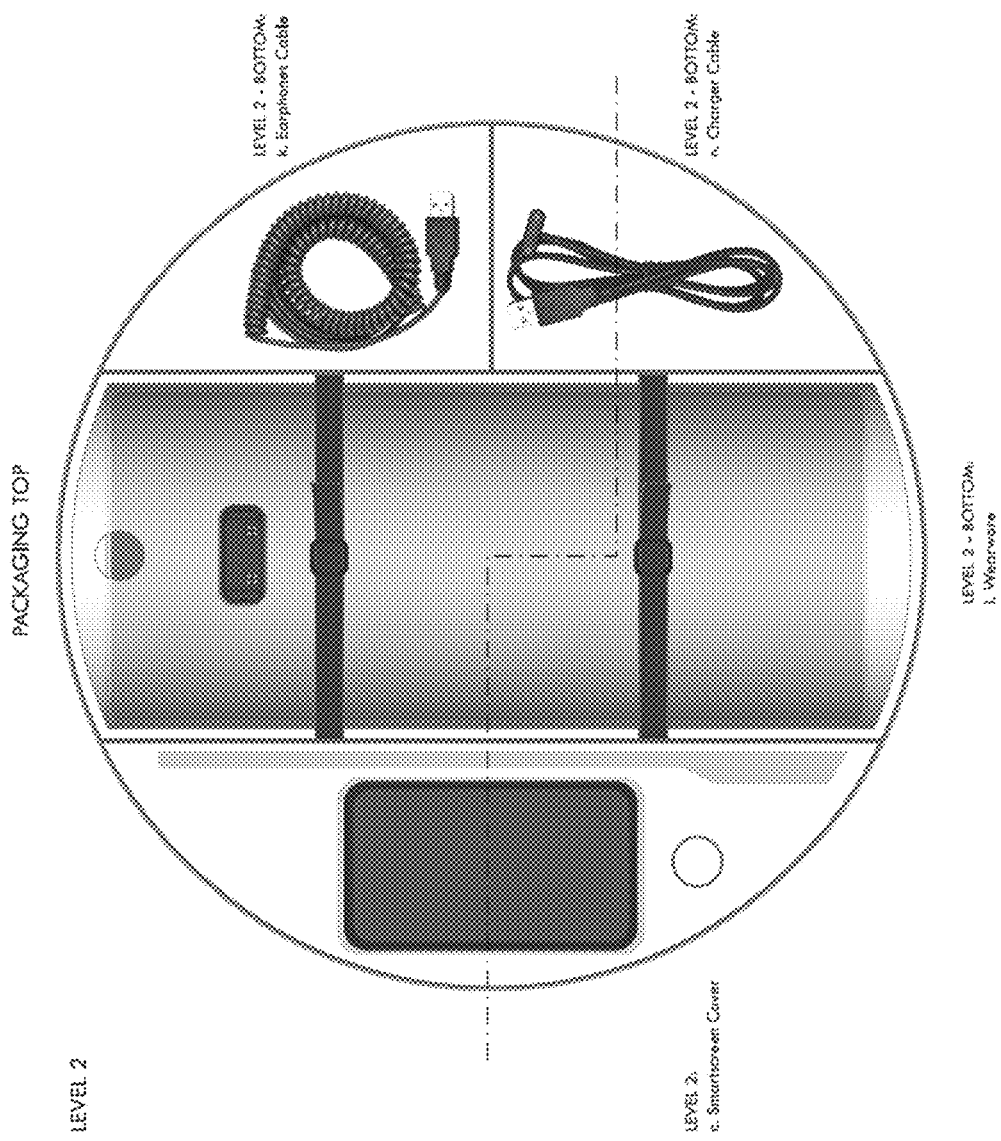
FIG. 8A schematically illustrate a top view of a calibration packaging apparatus with additional chambers.
Figure 8D:
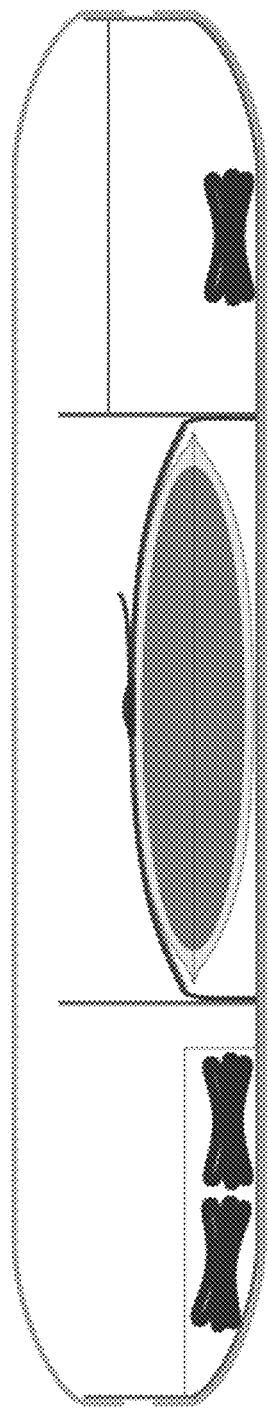
FIG. 8D schematically illustrate a side view of the multi-level calibration packaging apparatus of FIG. 8C.

FIGS. 8A and 8B schematically illustrate a top view and a side view of a calibration packaging apparatus with additional chambers. The apparatus can be configured to have more chambers to hold all the accessories of the physiological monitoring garment with integrated sensors. The additional chambers may hold an earphone, an earphone cable, a wristband, a camera, a charger cable, a USB adapter, a USB cable, etc. FIGS. 8C and 8D schematically illustrate a top view and a side view (respectively) of a multi-level calibration packaging apparatus. In some embodiments, the apparatus can be configured to have multiple levels such that the components can be stacked on top of the other components. In this way, the apparatus can be compact, easily fit into a suitcase and easily transport in the suitcase.

Also disclosed herein are methods of calibrating a physiological monitoring garment. The method can comprise placing a first physiological monitoring garment inside a first chamber in an inner region of a calibration packaging apparatus before or after connecting to a phone. As already mentioned, the garment can comprise a first plurality of position sensors, motion sensors, or position and motion sensors. The method can further comprise connecting a sensory management system (SMS) on the garment with a controller (e.g., phone, dedicated controller, etc.) held or to be held in another chamber of the inner region of the apparatus (or in some variations, through a cover of the apparatus). The method also includes securing the garment in place (e.g., using a securement/fixing retainer in the inner region to keep constant a plurality of relative distances between the first plurality of position sensors, motion sensors, or position and motion sensors during a calibration process). In some embodiments, the method further comprises using a separator in the inner region between the phone module and the garment, to shield magnetic energy between the phone module and the garment.

The method can include initiating a calibration process, which may be guided by the phone or embedded controller. The phone may direct the user in moving and rotating the apparatus in a predefined pattern and/or a random (user-selected) pattern; allowing all sensors to be calibrated simultaneously; and monitoring the calibration process by a feedback signal.

In some embodiments, the method can comprise initiating a calibration process through a smart screen of the phone module. In some other embodiments, the method can comprise initiating a calibration process through a controller in the inner region of the apparatus. In some embodiments, the method can comprise allowing all sensors to be calibrated simultaneously the phone module. In some other embodiments, the method can comprise allowing all sensors to be calibrated simultaneously by a controller in the inner region of the apparatus.

For example, a method of calibration of a physiological monitoring garment may include placing a first physiological monitoring garment inside a first chamber in an inner region of a calibration packaging apparatus. The garment may include a first plurality of position sensors, motion sensors, or position and motion sensors. The method further comprise connecting a sensory management system on the garment with a controller (e.g. phone) through a separator (and/or through the cover of the apparatus); using a fixing retainer in the inner region to keep constant a plurality of relative distances between the first plurality of position sensors, motion sensors, or position and motion sensors during a calibration process; and using a separator in the inner region between the phone module and the garment to shield magnetic energy between the phone and the garment. The method can comprise allowing a calibration process to be initiated; showing an instruction to move and rotate the apparatus on the smart screen; allowing the apparatus to be moved and rotated following the instruction; calibrating all sensors to be calibrated simultaneously; providing feedback of the calibration process; and indicating completion of the calibration process.

The controller controlling the calibration may be a phone which may execute instructions (e.g., software, firmware, hardware) that control the calibration and provide instructions to a user for moving the apparatus as part of the calibration.

As mentioned, the calibration may be controlled by a "calibration app" that is installed on the controller (e.g., communicating with an input such as a smart screen) or on a generic smartphone. The controller may be the controller directly connected to the garment (via the SMS) or the controller executing the instructions may be communicating (e.g., wirelessly or via cable) to a phone that is connected to the garment within or through the apparatus, for example, via a Bluetooth or Wi-Fi connection. Furthermore the "calibration app" may communicate the status of the calibration to the user, (progress bar/messages) and/or instructions to the user, and the also may communicate through the phone connected to the garment (if the app is running on a separate phone paired with the controller/phone connected to the garment) to communicate the status of the calibration to the user (e.g., blinking LED/vibration/sound).

In some variations, the user may also use only a phone connected directly to the garment (e.g., which may be referred to herein as a phone module) and may start the calibration with a specific combination of pressed buttons. Furthermore, the phone module may communicate the status of the calibration to the user (blinking LED/vibration/sound). For example, inside the packaging, the phone module may be connected to the garment and may communicate the status of the calibration to the user (blinking LED/vibration/sound). The entire packaging may be made of non-magnetic materials to avoid magnetic distortions.

As part of the instructions to the user, during calibration the user may be instructed to (and may) keep the calibration box apparatus away from any magnetic source (iron watches, iron wrist band, rings, coins . . . ). Thus, the user may be instructed to remove magnetic jewelry.

Prior to starting calibration, the user may connect the phone module directly to the garment; e.g., through a separator, as discussed above. Thus, a phone module (communications subsystem) may be mechanically attached to the garment. The phone module may then communicate the status of the calibration to a display/input (e.g., smart screen, including a generic smartphone) external to the calibration box with Bluetooth or Wi-Fi.

Figure 9A:
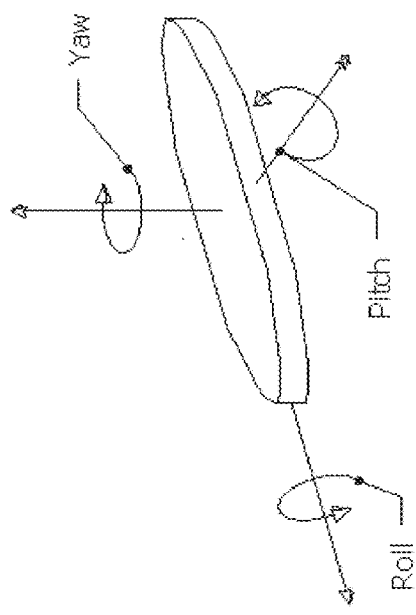
FIG. 9A shows an illustration of the various movements (including axes of movement) of any of the apparatuses described herein during calibration.
Figure 9B:
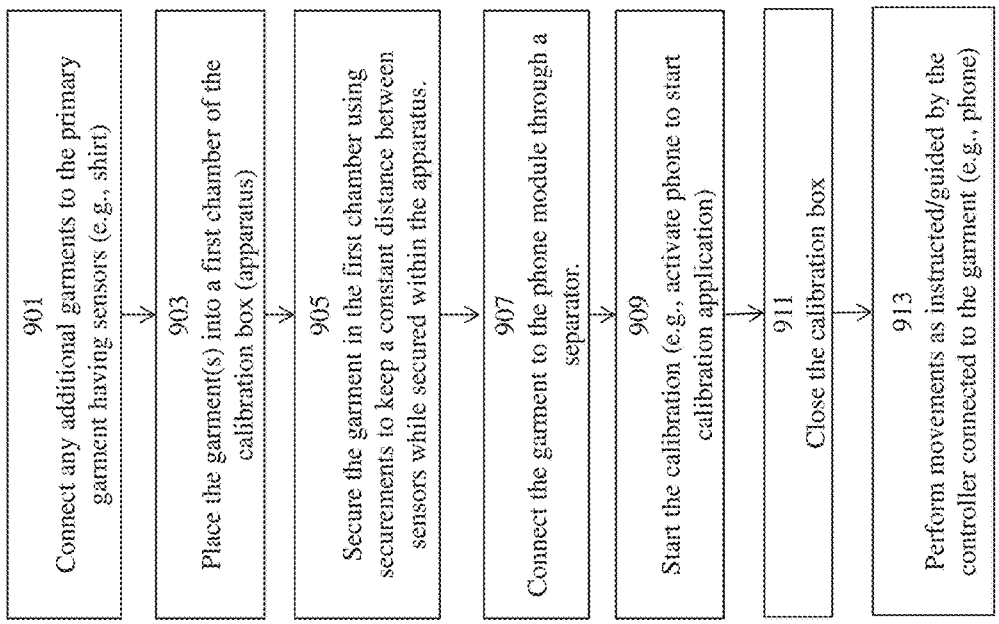
FIG. 9B is a schematic illustration of a method of calibration using any of the apparatuses described herein.

In operation, FIG. 9A shows the types of rotations that the user may perform to calibrate the garment using the apparatus. For example, the apparatus may be moved in one or more of yaw, pitch and roll. FIG. 9B describes one variation of a method of calibration using the apparatuses described herein.

In FIG. 9B, the user may first (optionally) connect any other sensor-containing garments to the primary garment to be calibrated 901. The user may then place the garment(s) into the appropriate chamber and/or region of the apparatus 903. In variations including a separator, the separator may be placed over the garment (which may be folded or otherwise compressed to fit into the apparatus); the separator and garment may be aligned so that the SMS input on the garment is aligned with the opening through the separator. The opening may include a rim, pin, or other guide portion to connect/interface with the SMS output easily. Securements (e.g., straps, etc.) may then be placed over the garment, and in some variations over the separator, to hold the garment in a fixed position relative to the apparatus 905. Thereafter, the phone module may be connected to the SMS of the garment through the separator 907. If a separate phone/controller (e.g., remote to the calibration box) such as a smartphone is being use, it may be initialized to begin calibration 909. The separate controller (smartphone, etc.) may be paired with the controller (phone module) in the calibration box prior to or after closing the box with the controller connected to the phone module 911. The phone module and/or remote controller (e.g., smartphone) may then instruct the user through the calibration movements, or may simply tell the user to being movements for calibration 913.

One or more markings on the calibration apparatus (e.g., arrows, etc.) may help to guide a user's movements during the calibration procedure. For example, in some variations, the user may be instructed to flip the calibration box, keeping the 0° marking in front. The user may then be instructed to rotate the calibration box to the next mark and repeat. When the user reach the 180° marking (e.g., following 8 flips and 8 rotations), the guided part of the calibration may be terminated, and the user may be asked to move the calibration box at random in the space. This is one example (including both guided/predetermined movements and a random/unguided set of movements) of the way that the user can perform a rapid calibration procedure. The arrows/markings on the apparatus are meant to guide the user's movements during the calibration procedure. For example, during the guided motions, the user may do a 360° flip of the "Calibration Box" keeping the 0° in front of him (roll rotation in FIG. 9A). The user should rotate the "Calibration Box" to the next mark (yaw rotation in the picture). The user may repeat this (roll and yaw movements) until reaching the "180°" (e.g., 8 flips and 8 rotations). At this point the guided part of the calibration may be terminated, and the user may be asked to move the calibration box at random in the space. The user may maintain the same body position during the calibration procedure and perform only rotations. The user may also keep the calibration box away from any magnetic source, as mentioned above (e.g., iron watches, iron wristband, rings, coins, etc.). The duration of the calibration may depend on the user's movements as the user follows the procedure. Generally, the procedure may take just a few minutes. In some variations, the apparatus (e.g., the application software) may include an automatic failure stop, if the calibration takes longer than a fixed time. During calibration, the application may monitor the calibration to determine the quality of the movements and/or calibration.

In general, the apparatuses described herein may accurately calibrate one or more garments including a plurality of sensors (e.g., a short-sleeved shirt, and/or shorts, tights, gloves, socks, balaclava, etc.).

Figure 10:
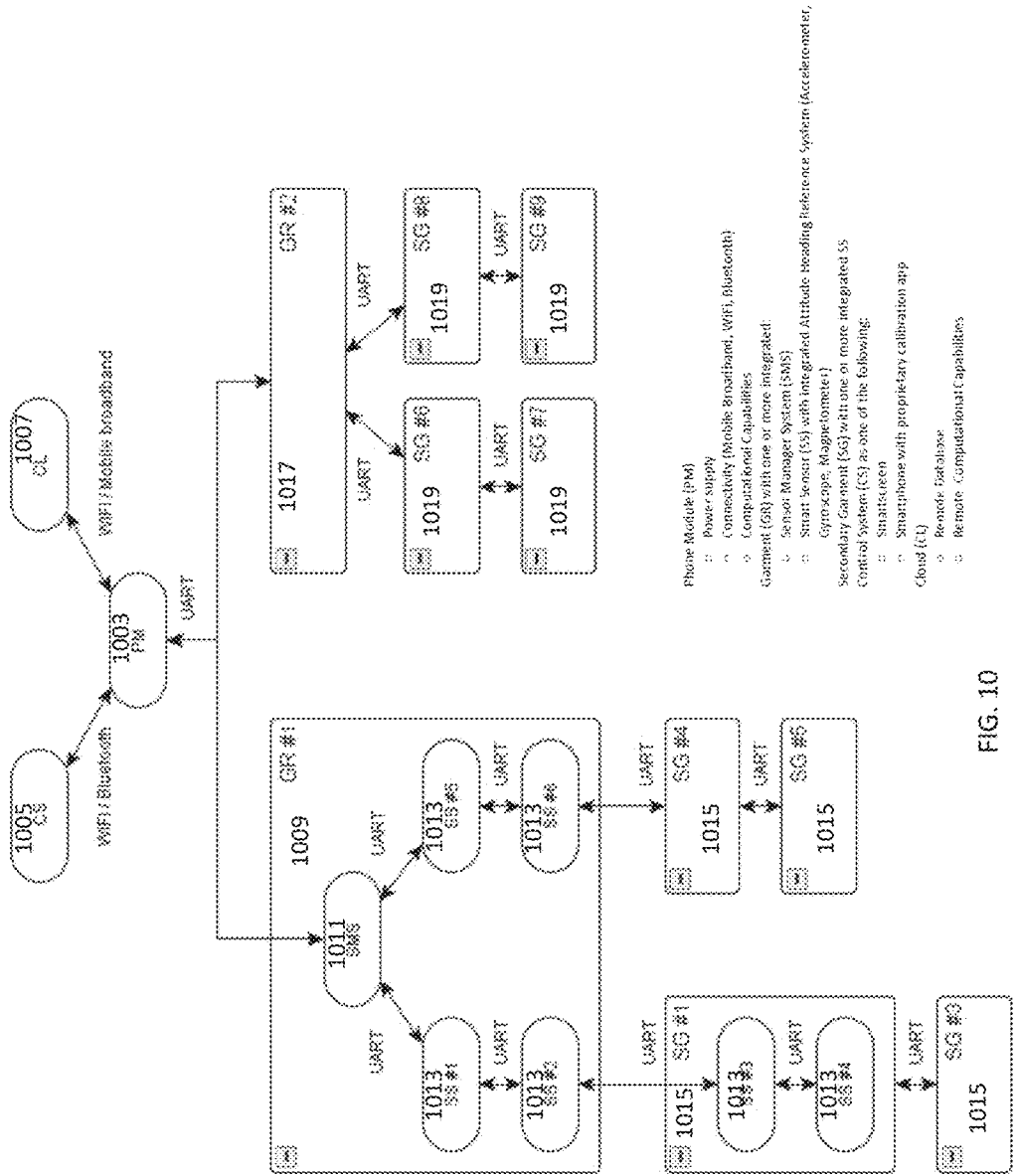
FIG. 10 illustrates one example of an architecture for communication between one or more garments (GR), including supplementary garments (SG) and sensors (SS) on the one or more garments and the cloud (CL) or control system (CS) (e.g., a smartphone or other remote processor) using a universal asynchronous receiver/transmitter (UART) of the calibration packaging for asynchronous serial communication; the data format and transmission speeds may be configurable.

FIG. 10 illustrates an exemplary architecture for a calibration apparatus as described herein. In FIG. 10, the apparatus may include or communicate with one or more processors that are part of: a communication subsystem (e.g., phone module or PM) 1003, a control system (e.g., a smartphone, smart screen, etc., typically including a processor running the the calibration application software) 1005, and/or a remote processor (cloud processor/server) 1007.

One or more of these processors may drive/guide the calibration using the calibration box (also referred to as a calibration storage container, etc.). Preferably the control system may be configured to execute control commands guiding the calibration, e.g., by running an application software. The apparatus may use a universal asynchronous receiver/transmitter (UART) to communicate between the various components, including the first garment (GR# 1) 1009, which may also include an SMS 1011 as discussed above, and a plurality of sensors (smart sensors 1013. Additional garments (e.g., supplementary or secondary garments 1015 including their additional sensors may also be connected either through the first garment 1009, or directly (e.g., second garment 1017, GR#2) and/or through additional garments 1019.

In any of the calibration apparatuses and methods, a processor, such as the communication subsystem 1003, may send and receive information and control commands to/from the garments and/or sensors in/on the garments, as shown in FIG. 10.

Figure 11A:
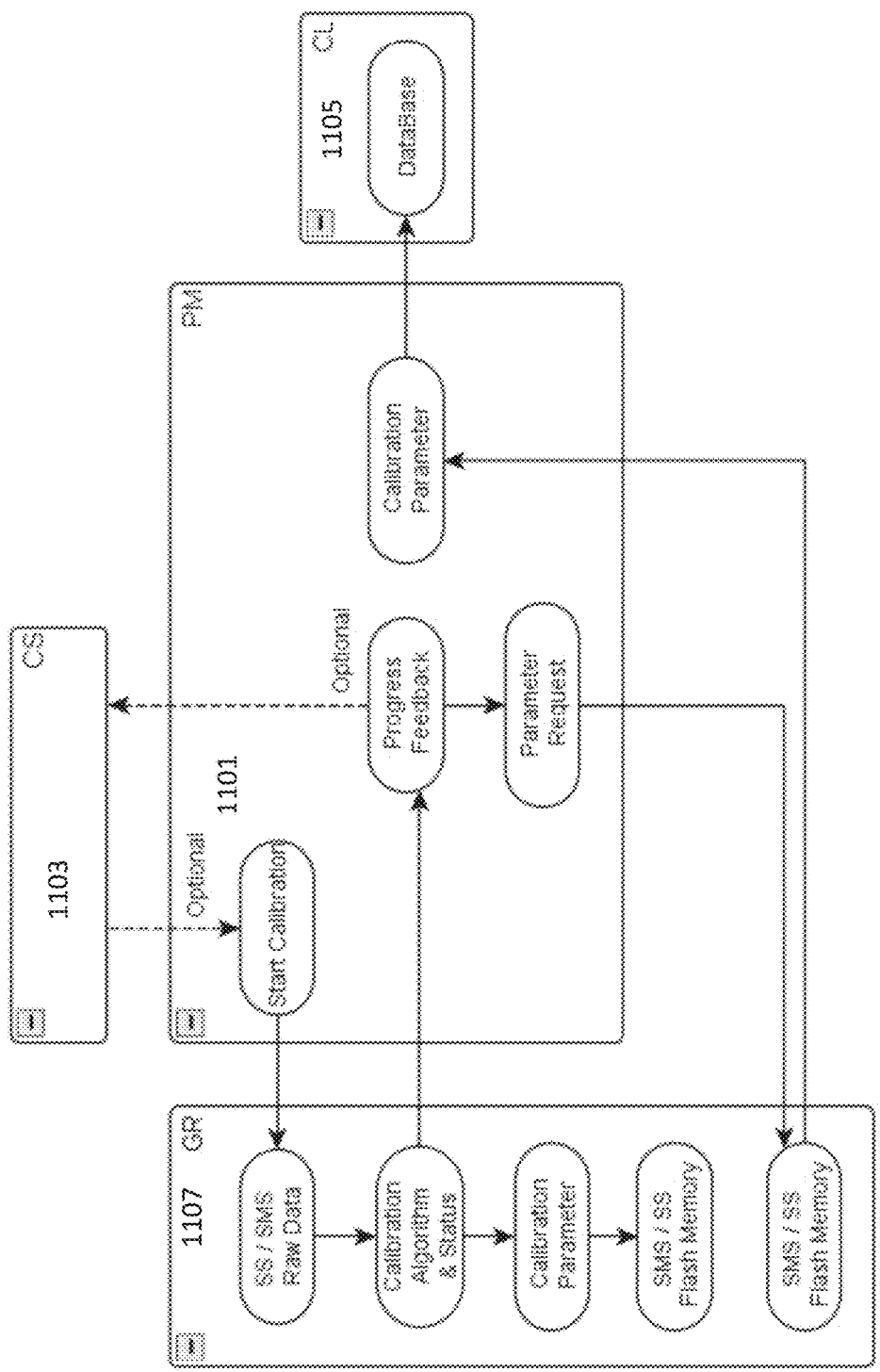
FIGS. 11A-11C are data flow diagrams illustrating possible data flows during calibration of one or more wearable physiological monitoring garment(s) as described herein.
Figure 11B:
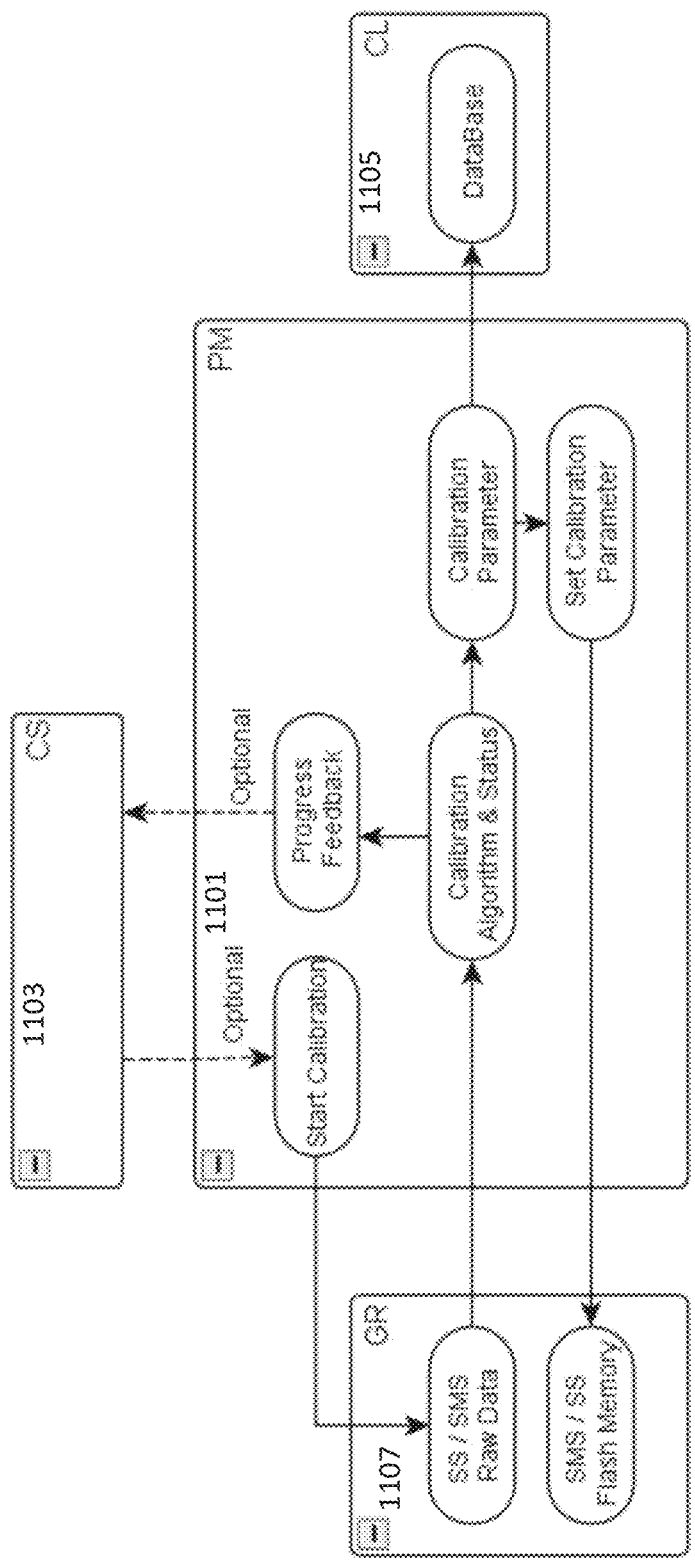
Figure 11C:
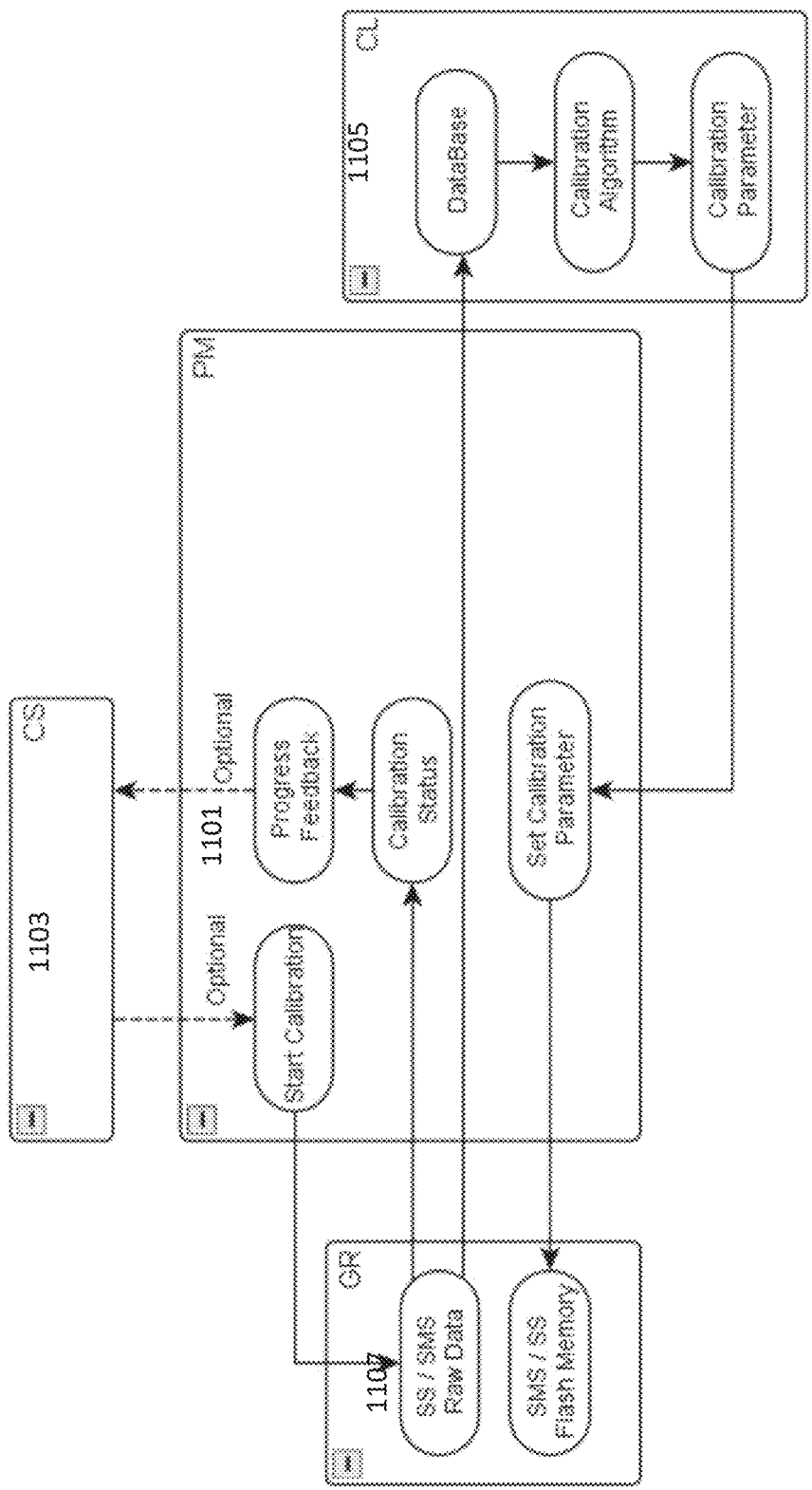

FIGS. 11A-11C illustrate exemplary data flows for any of the calibration apparatuses and methods described herein; these different data flows may coexist in the apparatuses and methods. For example, in FIG. 11A, the first exemplary data flow shows the communication between a communication subsystem (PM) 1101, one or more garments 1107, a control system 1103 and a remote site (cloud processor and/or server) 1105. In this example, the calibration procedure is started by the communication subsystem 1101 (or the control system 1003), and raw data may be collected from the SMS and/or the sensors, and may be elaborated by the sensors and/or SMS, and a calibration status may be provided to the communication subsystem (that could be forwarded also to the control system). Information may include commands to reset/calibrate the sensors, status of the sensor (s) (operational, error, etc.), output values of the sensors, etc. The information from the sensors and/or SMS may be used by the processor in the communication subsystem and/or control system to determine offset values and verify functioning of each sensors within predetermined operational parameters.

When calibration ends, the resulting calibration parameters may be stored into the SMS/sensor flash memory (including, but not limited to calibration offset values, and calibration relationships/curves, etc.). The completion of the calibration may be communicated to the communication subsystem (and eventually to control system). Finally, the calibration parameters could be sent to the remote site 1105.

Similarly, FIG. 11B illustrates another exemplary data flow between a communication subsystem (PM) 1101, one or more garments 1107, a control system 1103 and a remote site (cloud processor and/or server) 1105. In this example, the calibration procedure is started by the communication subsystem (or the control system), and raw data collected from sensors and/or SMS are sent and elaborated by the communication subsystem and a calibration status may be provided by the communication subsystem itself (that could be forwarded also to the control system). When the calibration finishes, the resulting calibration parameters may be stored into the SMS (and/or sensor) flash memory with a set calibration parameter request. The completion of calibration is eventually communicated to the control system. Finally, the calibration parameters could be sent to the remote site 1105.

In FIG. 11C, the calibration procedure is started by the communication subsystem 1101 (or the control system 1103), and raw data collected from sensors ("smart sensors") and/or SMS are sent through the communication subsystem to the remote site (cloud server/processor/memory) 1005. A calibration status may be provided by the communication subsystem itself (that could be forwarded also to the control system). When calibration completes, the resulting calibration parameters may be stored into the SMS and/or sensors in, e.g., a flash memory, with a set calibration parameter request. The completion of calibration is eventually communicated to the control system.

As mentioned above, in general the apparatuses described herein (systems, devices, etc.) may include a calibration housing (e.g., box, packaging, container, case, chamber, etc.) for holding a wearable physiological monitoring garments and allow it to connect to a processor running a calibration control program; the calibration control program ("app") may also form part of this apparatus. The calibration housing (e.g., calibration box) may be configured to prevent interference, e.g., may include magnetic shielding, and/or may be formed, including entirely formed, of a non-magnetic material, such as a non-non-ferromagnetic and non-diamagnetic material. In some variations the application software is specifically adapted to control the operation of calibration box and communicate (send/receive data and transmit commands) with sensors on one or more garments in the calibration housing, as well as coordinating the actions of a user in calibrating the sensors in the garment (e.g., instructing them to move the garment in a particular way in order to facilitate calibration).

In general, the calibration apparatuses and methods described herein may provide a user a simple way to perform multiple sensor calibration; the calibration apparatus may be used also as the product packaging and/or storage.

A calibration method using any of the calibration boxes described herein may include a communications subsystem (e.g., phone module or interface that is integrated into the garment and may be connected to a phone to couple the phone (e.g., smartphone) to the garment. Alternatively the garment may be configured to include a dedicated or integrated communications processor and may not need to couple directly to a phone (but may still, in some variations, communicate wirelessly with a phone). One or more garments may be placed and secured into the calibration box (each garment may include a plurality of sensors, such as those discussed above. A control system (e.g., smartphone) may optionally be used to perform the calibration and/or may be connected to the apparatus. The control system may be used to control the calibration state.

In general, a method of calibrating a garment having a plurality of sensors may include: connecting all of the garments to a phone module (e.g., communications subsystem) either directly or indirectly (e.g., through other garments), and typically mechanically connecting at least one garment to the phone module. The garments may be placed and secured within the calibration box, and the calibration box may be closed. The phone module (communications subsystem) may be turned on and (optionally) connected to the the control system (e.g., phone). In some variations, calibration may then begin, e.g., when turning on the phone module. Instructions may be provided to the user for one or more calibration types (or they may be simultaneously performed) and the phone module may send/receive data to/from the smart sensors and/or SMS for the garments, including all of the sensors of the garments. The control system (e.g., phone) running the calibration application (control logic) may be used to control the application state. See, e.g., FIG. 5B. The phone may be directly or indirectly (e.g., wirelessly) communicating with the sensor module.

The calibration duration may depend on the type of sensor and the appropriateness of the user's movements in following the procedures (e.g., instructions of the control system/phone). Generally, if it is performed correctly, the calibration procedure may take a few minutes (e.g., <3 minutes), and may automatically stop when it takes longer than a fixed time (e.g., 3 minutes, 4 minutes, 5 minutes, 6 minutes, 7 minutes, 8 minutes, 10 minutes, etc.). The system may then ask the user to repeat the procedure.

EXAMPLE 1

Calibration

A calibration box may be maintained in fixed orientation during all or a portion of a calibration process. For example, this could be fulfilled by one of the following: positioning a polyhedron-shaped calibration box (e.g., having one or more flat sides, e.g., a dodecahedron, octagon, etc., with numbered faces) on one or more sides; and/or providing a vertical stand 1201 (see, e.g., FIGS. 12A and 12B) to hold the calibration box in a fixed configuration for a predetermined amount of time. The calibration box may have numbered directions markers thereon.

For example, to calibrate one or more accelerometers of a garment using a calibration apparatus including a calibration box that is a polyhedraon (e.g., having multiple flat slides and a front and back), the user may place the calibration box, after storing the garment(s) therein, on a flat surface in all the orientations as instructed by the application software by following the numerical sequence provided, where the sequences may be correlated to markings (e.g., symbols, alphanumeric markings, etc.) on the calibration box. After placing the box on a side, a predetermined waiting time may be observed, between each instructed movement, as provided according to the phone module and/or the control system.

In some variation, the calibration box may be held by a stand 1201 or holder in the instructed positions, as shown in FIGS. 12A and 12B. In such cases, the vertical stand may be placed on a flat surface and the calibration box placed in all the instructed orientations, e.g., aligning the directions markers, following the sequence provided by the calibration application software.

When calibrating one or more gyroscope sensors, the calibration box may be maintained in a fixed position during the calibration process. For example, the calibration box may be placed on a flat surface while the user waits to receive instructions and/or feedback from the calibration application software (e.g., operating on the phone module or control system).

Figure 13D:
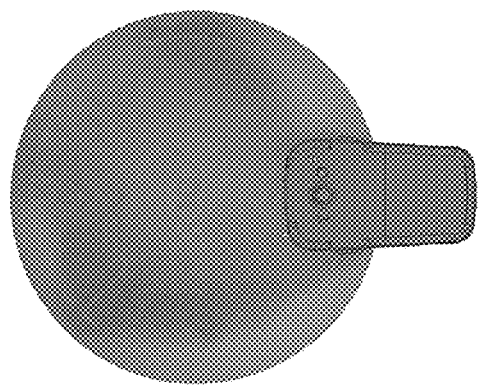

When calibrating one or more magnetometers in the garments, the calibration box may protect the garment (and sensors) from errors during calibration. For example, the calibration box may be made entirely from non-ferromagnetic materials and kept away from any magnetic source. For example, FIG. 13A illustrates one example in which the calibration box includes an aperture 1301 in the front shell. In this configuration the phone module 1305 may be held outside of the calibration box, or exposed through the aperture, thus the phone module may be kept separate from the garment within the box, as shown in FIG. 13B. In general the garment may be held in a fixed position relative to the phone module.

During calibration, the calibration box may be moved in multiple orientations. Thus, the calibration box may have a shape that provides easy and comfortable handling during the calibration procedure. For example, as shown in FIGS. 13A-13D the calibration box has a rounded shape (e.g., is disc-shaped). In other variations, the calibration box is polygonal, as mentioned above.

Figure 14D:
FIG. 14A is an example of a display on a control system (e.g., phone) running calibration software (e.g., an app) and indicating progress of the calibration procedure; the app may also cause the apparatus to display and/or describe calibration instructions to the user, including moving the calibration box through various motions, as shown in FIGS. 14B, 14C and 14D.
Figure 14C:
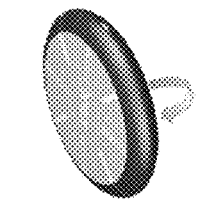
Figure 14B:
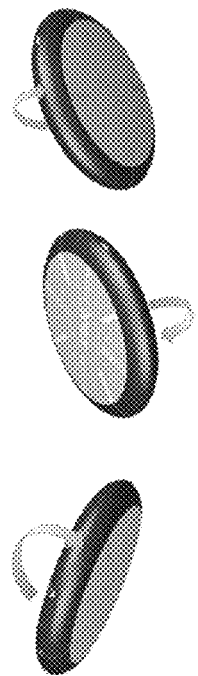

During calibration, and particularly during calibration of some of sensors, including the magnetometer and other sensors, the apparatus may instruct the user to move the calibration box in a random pattern for a period of time indicated by the apparatus. FIG. 14A-14D illustrates this, showing (in FIG. 14A) the calibration control software (app, e.g., a non-transitory machine-readable medium that stores instructions that when executed by a processor cause the apparatus to perform the calibration as described herein) indicating the progress of calibration. FIGS. 14B-14D illustrate the movement of the apparatus in various directions (shown by arrows). This motion may be continued until the control software (e.g., running on the phone module or control system) indicate that calibration is complete, or time out. During this procedure, the user may: keep the calibration box away from any magnetic source (iron watches, iron wrist band, rings, coins, etc.); maintain the same position during the calibration procedure; perform random rotations; and avoid jerky movements. The apparatus may indicate if any of these conditions are not met.

EXAMPLE 2

Multi-Level Calibration Box

Figure 15B:
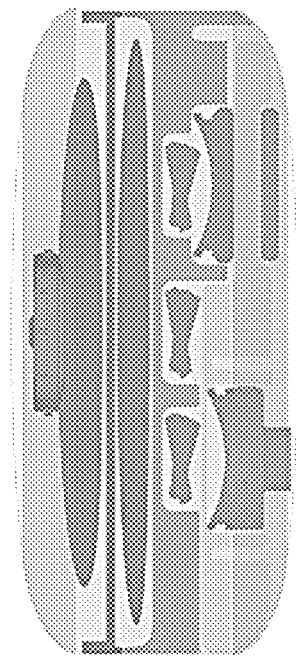
FIGS. 15A and 15B illustrates views of another variation of a calibration box, as described herein.
Figure 15A:
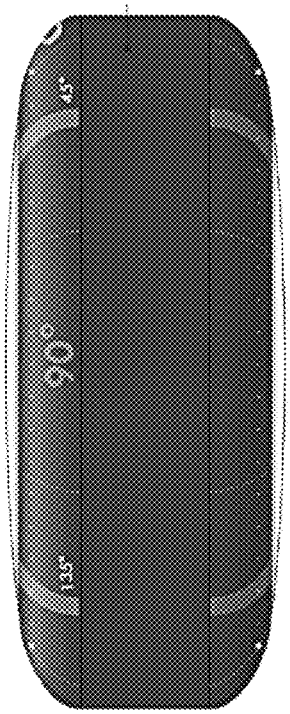
Figure 16B:
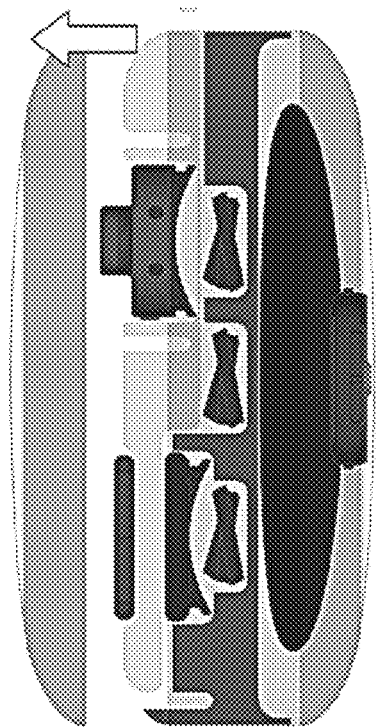
FIGS. 16A and 16B illustrate a calibration box such as the one shown in FIGS. 15A and 15B with the top (FIG. 16A) or the bottom (FIG. 16B) removed.
Figure 16A:
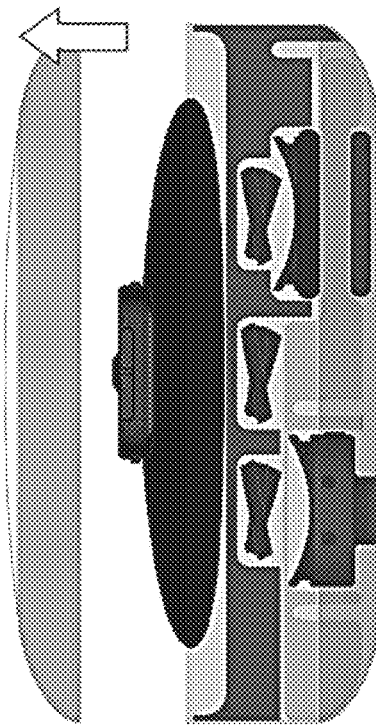
Figure 17:
FIG. 17 is an example of a calibration box having an additional layer added.

FIGS. 15A and 15B illustrate an example of a calibration box having multiple levels, as described herein. In FIG. 15A, the calibration box is also cylindrical, with rounded sides, and includes markings on the sides. FIG. 15B shows a view in which the calibration box of FIG. 15A has been made transparent. In this example, there are multiple, stacking, layers that may hold a variety of different garments, at least some of which include a plurality of sensors. FIGS. 16A and 16B illustrate the apparatus of FIGS. 15A and 15B in which the top (FIG. 16A) or bottom (FIG. 16B) have been removed to expose different regions within the apparatus. Thus, the apparatuses described herein may be saleable, and may include additional 'rings' or levels, and specific foams to form sub compartments within the inner volume, as shown in FIGS. 15B and 16A-16B. FIG. 17 is an example showing an additional level 1701 added to the compartment to hold additional garment(s). As mentioned, these calibration boxes may be easy to transport, and may include a handle, wheels, etc.

Figure 14A:
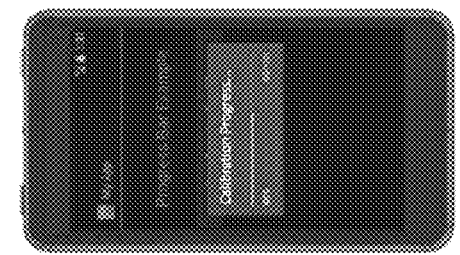

The apparatuses described herein may provide quick and easy feedback to a user about the calibration progress state, as shown in FIG. 14A. The start and the stop of the calibration procedure may be controlled by the software, e.g., running on the control system (e.g., smartphone), which may communicate with the phone module (e.g., communications subsystem) via Bluetooth or Wi-Fi. Furthermore, in this configuration, the control system may communicate the status of the calibration to the user via a progress bar/messages. The phone module may also communicate the status of the calibration to the user, e.g., via a blinking LED/vibration/sound, as shown in FIG. 5A.

In some variations the user may also use only the phone module for calibration, without using a control system (such as a phone). In this case, the phone module may be used to start the calibration with a specific combination of pressed button(s). The PM may also itself communicate the status of the calibration to the user, e.g., via a blinking LED/vibration/sound, etc.

In general, the calibration box may not have any embedded electronics. The apparatus may generally provide for simultaneous calibration of all of the sensors/SME components in garments within the calibration box. The garment can be connected with other garments (e.g., supplementary garments, secondary garments, etc.) such as shirts, thighs, balaclavas, gloves, etc., during a calibration procedure so that all the sensors/SMS in all different garments can be calibrated at the same time. Data obtained with calibration procedure may be directly processed by the phone module or by the garment (e.g., in one or more on-board calibration processors) to obtain calibration parameters. Data obtained with calibration may be sent to a remote (e.g., cloud) processor/memory/server through the connectivity of the phone module (e.g., via Mobile Broadband, Bluetooth, Wifi, etc.) which may provide enhanced computational power.

When calibrating an accelerometer and magnetometer, the apparatus may constrain the positioning of the garment(s) inside the calibration box, as mentioned above. For example, the apparatus may include one or more ties to keep constant the position and relative distances between the sensors/SMS during the calibration process. This may be important to avoid undesired collision that could happen if the sensors/SMS were free to move into the calibration box. Similarly, as mentioned above, when calibrating sensors including magnetosenors, it may be beneficial to keep the garment separate from the phone module (communications sub-system) to which it is physically coupled; thus an aperture through the calibration box may keep the phone module fixed relative to the garment and calibration box, while allowing connection and preventing magnetic distortions.

The comfortable form factor of the calibration box may also allow easy manipulation of the box to facilitate rotation, which may be especially relevant for magnetometer calibration in which smooth rotation in all directions may be applied. Although in some variations the calibration box may include markings (e.g., embossed arrows) to guide the user's movements during the calibration procedure, this may not be necessary, as the user may randomly move the calibration box.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A calibration packaging apparatus for simultaneously calibrating a plurality of position sensors, motion sensors, or position and motion sensors of a physiological monitoring garment that is held within the apparatus, the apparatus comprising:
   a housing, the housing comprising:
      a securement within the housing configured to hold the physiological monitoring garment so that the separation between each of the sensors of the plurality of position sensors, motion sensors, or position and motion sensors remains constant as the housing is moved; and
      a separator within the housing dividing the housing into a first region for holding the physiological monitoring garment and a second region for holding a phone, wherein the separator comprises an opening therethrough for connecting the phone to a connector on the physiological monitoring garment;
      wherein the housing and the separator are made entirely of non-magnetic materials, and
   a non-transitory machine-readable medium that stores instructions, which, when performed by a processor, cause the processor to:
      communicate with the plurality of sensors to receive raw data from the sensors;
      display instructions to position the calibration packaging in a plurality of positions for a period of times; and
      transmit calibration information on each sensor.

2. The apparatus of claim 1, further comprising a pair of reference markings an outer peripheral surface region of the housing that are separated by 90 degrees.

3. The apparatus of claim 1, further wherein the separator is in the inner region and configured to be positioned between a phone and the first physiological monitoring garment.

4. The apparatus of claim 1, wherein the separator is configured to shield magnetic energy between a phone and the first physiological monitoring garment.

5. The apparatus of claim 1, further comprising a plurality of markings.

6. The apparatus of claim 1, further comprising an ergonomic hand-grip configured to facilitate rotation.

7. The apparatus of claim 6, wherein the ergonomic hand-grip comprises rubber.

8. The apparatus of claim 6, wherein the ergonomic hand-grip comprises soft-touch plastic.

9. The apparatus of claim 1, wherein the securement comprises at least one tie.

10. The apparatus of claim 1, wherein the securement comprises at least one strap.

11. The apparatus of claim 1 further comprising a flat bottom surface that is configured to slide open.

12. The apparatus of claim 1 further comprising a controller configured to control the calibration process.

13. The apparatus of claim 1 further comprising a phone having a controller, wherein the phone is configured to attach to an sensory management system (SMS) on the physiological monitoring garment through the separator and control the calibration process.

14. The apparatus of claim 1 further comprising an output in the inner region configured to provide feedback of the calibration process.

15. The apparatus of claim 1 further configured to be connected to a cloud through the phone.

16. The apparatus of claim 1 further configured to be a docking station.

17. The apparatus of claim 1 further comprising an additional chamber configured to hold at least one of an earphone and an earphone cable, a wristband, a camera, a charger cable, a USB adapter and a USB cable.

18. The apparatus of claim 1, further comprising a transparent cover.

19. The apparatus of claim 1, wherein a cross-section of the apparatus is circular with a diameter between about 10 cm to about 50 cm.

20. The apparatus of claim 1, wherein the apparatus is formed primarily of a molded plastic.

21. A calibration packaging apparatus for a physiological monitoring garment, the apparatus comprising:
   an inner region for storage;
   a cover configured to cover the inner region;
   a first physiological monitoring garment comprising a first plurality of position sensors, motion sensors, or position and motion sensors;
   a first chamber in the inner region configured to hold the first physiological monitoring garment;
   a phone;
   a second chamber in the inner region configured to hold the phone;
   a separator between the first chamber and the second chamber, wherein the separator comprises a sheet extending through the inner region to shield magnetic energy between the phone and the garment;
   an opening through the separator through which the phone may connect to a sensory management system in the first physiological monitoring garment;
   a retainer in the inner region configured to secure the first physiological monitoring garment within the inner region so as to maintain the relative distances between the first plurality of position sensors, motion sensors, or position and motion sensors during a calibration process; and
   wherein the entire first chamber, second chamber and separator are made of non-ferromagnetic and non-diamagnetic materials so that the first plurality of position sensors, motion sensors, or position and motion sensors may be accurately and simultaneously calibrated.

22. The apparatus of claim 21, further comprising orientation markings on the cover configured to show a specific positions.

23. The apparatus of claim 22, wherein the phone is configured to perform automatic calibration parameter computation.

24. The apparatus of claim 22, wherein the phone comprises an LED configured to provide feedback of the calibration process.

25. The apparatus of claim 22, wherein the phone comprises a screen configured to provide feedback of the calibration process.

26. The apparatus of claim 22, further comprising a third chamber configured to hold a second physiological monitoring garment having a second plurality of position sensors, motion sensors, or position and motion sensors, wherein the first garment is configured to be connected with the second garment during the calibration process such that the first plurality and the second plurality of position sensors, motion sensors, or position and motion sensors are calibrated at the same time.

27. The apparatus of claim 22, wherein the first chamber and second chamber are configured to hold the phone at least 2 cm from any of the first plurality of position sensors, motion sensors, or position and motion sensors.

28. A method of calibrating a physiological monitoring garment, the method comprising:
   placing a first physiological monitoring garment inside a first chamber in a first inner region of a calibration packaging apparatus, the garment comprising a first plurality of position sensors, motion sensors, or position and motion sensors;
   connecting a sensory management system on the garment with a phone that is in a second chamber of the calibration packaging apparatus;
   securing, using a retainer, the first physiological monitoring garment in the first inner region to keep constant a plurality of relative distances between all sensors of the first plurality of position sensors, motion sensors, or position and motion sensors during a calibration process; and
   shielding magnetic energy between the phone and the garment using a separator in the inner region between the phone and the garment and
   simultaneously calibrating the first plurality of position sensors, motion sensors, or position and motion sensors by moving and rotating the apparatus by moving the apparatus through a plurality of motions.

29. The method of claim 28 further comprising monitoring the calibration process by a feedback signal.

30. The method of claim 29, further comprising initiating a calibration process using the phone.

31. The method of claim 29, further comprising initiating a calibration process using a controller in the inner region of the apparatus.

32. The method of claim 29, wherein moving and rotating the apparatus following an instruction including following instructions presented by the phone.

33. The method of claim 29, wherein moving and rotating the apparatus comprises following instruction presented on a display of the phone visible through the calibration apparatus.

34. A method of calibrating a physiological monitoring garment, the method comprising:
   placing a first physiological monitoring garment inside a first chamber in an inner region of a calibration packaging apparatus, the garment comprising a first plurality of position sensors, motion sensors, or position and motion sensors;
   connecting a sensory management system on the garment with an output in another chamber of the inner region or through a cover;
   using a fixing retainer in the inner region to keep constant a plurality of relative distances between the first plurality of position sensors, motion sensors, or position and motion sensors during a calibration process; and
   using a separator in the inner region between the phone and the garment, to shield magnetic energy between the phone and the garment;
   allowing a calibration process to be initiated;
   showing an instruction to move and rotate the apparatus on the smart screen;
   allowing the apparatus to be moved and rotated following the instruction;
   calibrating all sensors to be calibrated simultaneously;
   providing feedback of the calibration process; and
   indicating completion of the calibration process.

35. The method of claim 34, wherein initiating a calibration process including initiating a calibration process through a smart screen of the phone.

36. The method of claim 35, wherein initiating a calibration process including initiating a calibration process through a controller in the inner region of the apparatus.

37. The method of claim 35, wherein calibrating all sensors to be calibrated simultaneously including calibrating all sensors to be calibrated simultaneously by the phone.

38. The method of claim 35, wherein calibrating all sensors to be calibrated simultaneously including calibrating all sensors to be calibrated simultaneously by a controller in the inner region of the apparatus.

* * * * *